United States Patent [19]
Hazato et al.

[11] Patent Number: 4,788,319
[45] Date of Patent: Nov. 29, 1988

[54] NOVEL ISOCARBACYCLINS AND PROCESSES FOR PRODUCTION THEREOF

[75] Inventors: Atsuo Hazato; Toshio Tanaka, both of Hino; Noriaki Okamura, Chofu; Kiyoshi Bannai, Hino; Kurozumi, Seizi, Kokubunji; Suzuki, Masaaki, Nagoya; Noyori, Ryoji, Aichi, all of Japan

[73] Assignee: Teijin Limited, Tokyo, Japan

[21] Appl. No.: 44,957

[22] Filed: May 1, 1987

[30] Foreign Application Priority Data

May 1, 1986 [JP] Japan ................................. 61-99470
Sep. 19, 1986 [JP] Japan ............................... 61-219117
Sep. 19, 1986 [JP] Japan ............................... 61-219118
Sep. 19, 1986 [JP] Japan ............................... 61-219119

[51] Int. Cl.$^4$ ...................................... C07C 147/107
[52] U.S. Cl. .................... 560/011; 562/427; 556/428; 549/427
[58] Field of Search ................. 560/011; 562/427; 556/428; 549/427

[56] References Cited

PUBLICATIONS

Tetrahedron Letters, vol. 25, No. 44, pp. 5087–5090, 1984; T. Mase et al.
Tetrahedron Letters, vol. 27, No. 7, pp. 845–846, 1986; D. Ferroud et al.
Tetrahedron Letters, No. 36, 1972, pp. 3815–3817, Bagli et al.

Primary Examiner—Paul J. Killos
Attorney, Agent, or Firm—Wenderoth, Lind & Ponack

[57] ABSTRACT

A novel isocarbacyclin which is a compound represented by the following formula

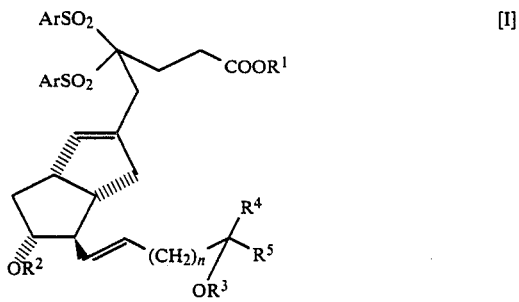

wherein $R^1$ represents a hydrogen atom, or a $C_1$–$C_4$ alkyl or alkenyl group; $R^2$ and $R^3$ are identical or different and each represents a hydrogen atom, a tri($C_1$–$C_7$)hydrocarbon-silyl group or a group forming an acetal linkage together with the oxygen atom of the hydroxyl group; $R^4$ represents a hydrogen atom, a methyl group or a vinyl group; $R^5$ represents an unsubstituted linear or branched $C_3$–$C_8$ alkyl group which may be interrupted by an oxygen atom, a substituted linear or branched $C_1$–$C_5$ group in which the substituent is a $C_1$–$C_6$ alkoxy group or a phenyl, phenoxy or $C_3$–$C_{10}$ cycloalkyl group which may be substituted further, a phenyl group which may be substituted, a phenoxy group which may be substituted, or a $C_3$–$C_{10}$ cycloalkyl group which may be substituted; n is 0 or 1; and Ar represents a substituted or unsubstituted phenyl group, its enantiomorph, or a mixture both in an arbitrary ratio.

7 Claims, No Drawings

NOVEL ISOCARBACYCLINS AND PROCESSES FOR PRODUCTION THEREOF

This invention relates to novel isocarbacyclins and processes for production thereof.

More specifically, this invention relates to novel isocarbacycline derivatives which are intermediates for synthesis of 9(O)-methano-$\Delta^{6(9\alpha)}$-prostaglandin $I_1$ (isocarbacyclin) resulting from substitution of a methine group (—HC=) for the oxygen atoms at the 6,9-positions of prostaglandin $I_1$, and to processes for production thereof.

Prostaglandin is a local hormone produced mainly in the inner vascular wall of the artery in an animal. It is an important factor for controlling the cell functions of the living body by its strong physiological activities such as platelet aggregation inhibitory activity and vasodilating activity. Attempts have been made to use it directly as a medicine (Clinical Pharmacology of Prostacyclin, Raven Press, N.Y., 1981).

Natural prostacyclin readily loses activity under neutral or acidic conditions because it has a very hydrolyzable enol ether linkage in the molecule. It is therefore undesirable as a medicine because of its chemical instability. Thus, extensive investigations have been conducted worldwide on chemically stable synthetic prostacyclin derivatives having the same physiological activities as the natural prostacyclin.

A derivative derived by substituting a methylene group for the oxygen atoms at the 6,9-position of prostacyclin, i.e. 9(O)-methanoprostacyclin (cabacyclin), is known to have fully satisfactory chemical stability (Prostacyclin, J. R. Vane and S. Bergstrom, Eds., Raven Press, N.Y., pp. 31–4). It is expected to be used as a medicine. However, 6,9 (O)-methanoprostacyclin is not entirely desirable because its biological activities are weaker than those of natural prostacyclin and the selectivity of its action is not specific.

It was recently discovered that isocarbacyclins, i.e. 9(O)-methano-$\Delta^{6(9\alpha)}$-prostaglandins $I_1$, which are a kind of double bond isomers of carbacyclin, show the strongest platelet aggregation inhibiting activity among the prostacyclin analogs, and they are expected to be applied as medicines [Ikegami et al., Tetahedron Letters, 24, 3493 (1983), and Japanese Laid-Open Patent Publication No. 137445/1984].

The following methods have previously been known for the production of 9(O)-methano-$\Delta^{6(9\alpha)}$-prostaglandin $I_1$ (isocarbacyclin).

(1) Ikegami et al., Tetrahedron Letters, 24, 3493 (1983) and Chemistry Letters, 1984, 1069:

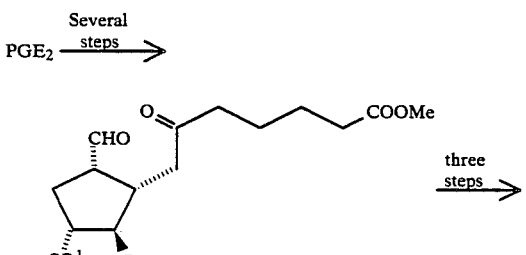

(2) Ikegami et al., Tetrahedron Letters, 24, 3497 (1983):

(3) Ikegami et al., J. Chem. Soc., Chemical Communications, 1984, 1602:

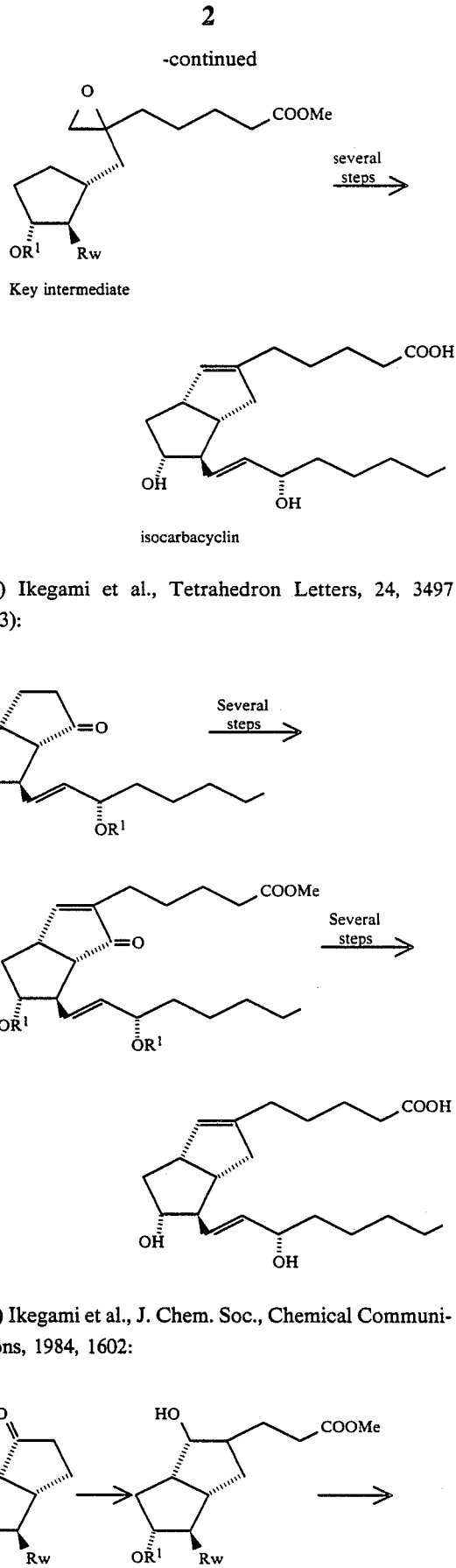

-continued

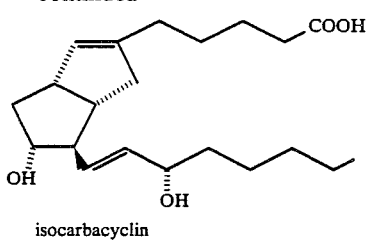
isocarbacyclin (4) Shibasaki et al., Tetrahedron Letters, 25, 5087 (1984):

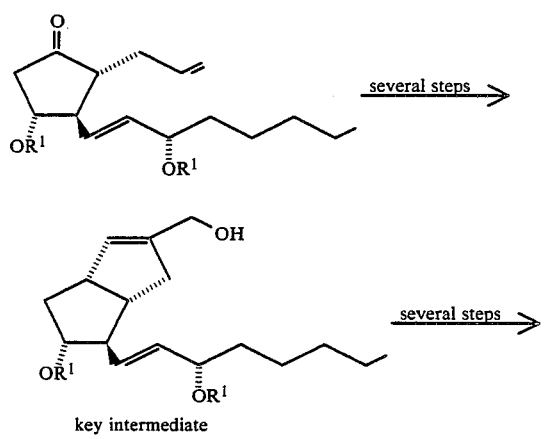
key intermediate isocarbacyclic (5) Shibasaki et al., Tetrahedron Letters, 25, 1067 (1984):

PGE₂ ⟶

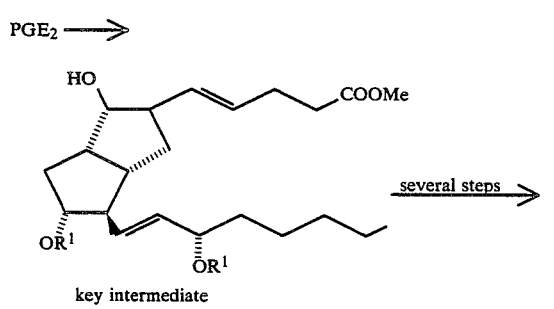
key intermediate

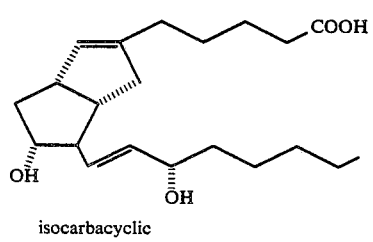
isocarbacyclic (6) Kojima et al., Chem. Pharm. Bull., 32, 2866 (1984):

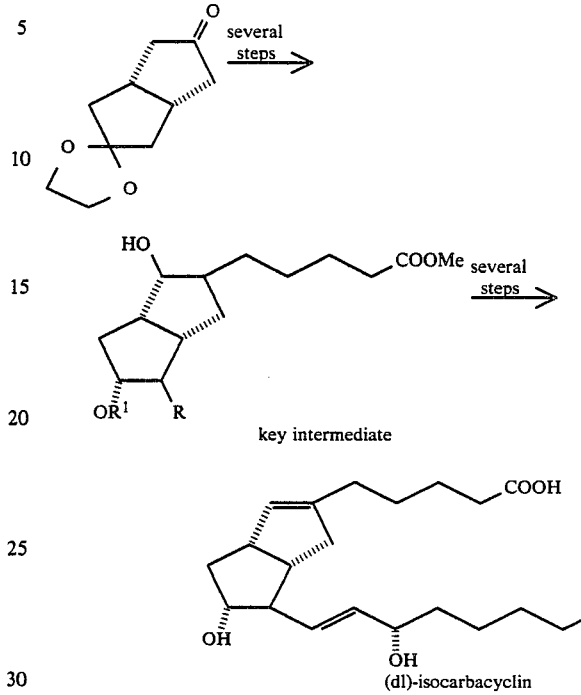
key intermediate (dl)-isocarbacyclin (7) Kojima et al., Japanese Laid-Open Patent Publication No. 28943/1985:

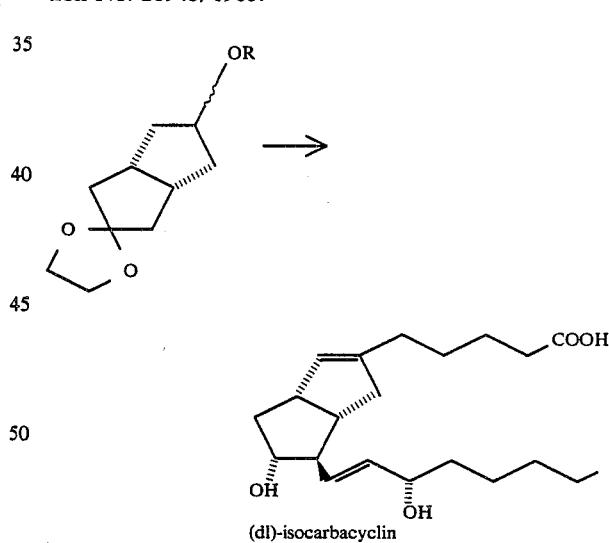
(dl)-isocarbacyclin

Among these seven methods, methods (1) and (5) cannot be said to be industrially feasible since they start from PGE₂, require several steps to convert it to a key intermediate and further require several steps to obtain the desired isocarbacyclin.

Methods (2) and (3) require many steps to obtain the corresponding starting materials and key intermediates from expensive Corey's lactone, and the overall yield of the final product is not high. Hence, these methods are not entirely advantageous for industrial practice.

Methods (6) and (7) give the final products only in DL-form, and are not desirable for giving products intended for pharmaceutical application.

In method (4), the starting material can be easily obtained from optically active (R)-4-hydroxy-2-cyclopentenone by the method of the present inventors (Japanese Laid-Open Patent Publication No. 155116/1982), and the conversion of the starting material into a key intermediate can be carried out without any problem in industrial practice. This method, however, encounters various difficulties in its route from the key intermediate to the final isocarbacyclin, and is not industrially feasible. For example, the use of an organic mercury compound is necessary, or the regio specificity is lost. Moreover, since an inseparable by-product occurs, the total yield of the final product is low.

In an attempt to overcome these difficulties, the present inventors have made extensive investigations on 9(O)-methano-$\Delta^{6(9\alpha)}$-prostaglandins $I_1$ (isocarbacyclins) and a process for production thereof. These investigations have now led to the present invention.

According to this invention, there are provided a compound represented by the following formula [I]

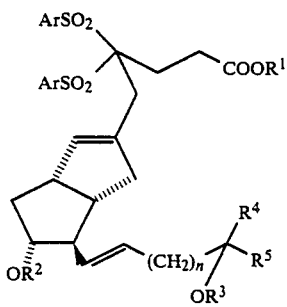

wherein $R^1$ represents a hydrogen atom, or a $C_1$-$C_4$ alkyl or alkenyl group; $R^2$ and $R^3$ are identical or different and each represents a hydrogen atom, a tri($C_1$-$C_7$-)hydrocarbon-silyl group or a group forming an acetal linkage together with the oxygen atom of the hydroxyl group; $R^4$ represents a hydrogen atom, a methyl group or a vinyl group; $R^5$ represents an unsubstituted linear or branched $C_3$-$C_8$ alkyl group which may be interrupted by an oxygen atom, a substituted linear or branched $C_1$-$C_5$ alkyl group in which the substituent is a $C_1$-$C_6$ alkoxy group or a phenyl, phenoxy or $C_3$-$C_{10}$ cycloalkyl group which may be substituted further, a phenyl group which may be substituted, a phenoxy group which may be substituted, or a $C_3$-$C_{10}$ cycloalkyl group which may be substituted; n is 0 or 1; and Ar represents a substituted or unsubstituted phenyl group, its enantiomorphs, or a mixture said compound and its enantiomorph in an arbitrary ratio; and processes for production thereof.

In formula [I], $R^1$ represents a hydrogen atom or an alkyl or alkenyl group having 1 to 4 carbon atoms. Examples of the $C_1$-$C_4$ alkyl group are methyl, ethyl, propyl and butyl groups. Examples of the $C_1$-$C_4$ alkenyl group are 2-propene and 3-butene groups. Among these, methyl and 2-propene groups are preferred.

In formula [I], $R^2$ and $R^3$ are identical or different, and each represents a hydrogen atom, a tri($C_1$-$C_7$)hydrocarbon-silyl group, or a group forming an acetal linkage together with the oxygen atom of the hydroxyl group.

Examples of the tri($C_1$-$C_7$)hydrocarbon-silyl group include tri($C_1$-$C_4$)alkylsilyl groups such as trimethylsilyl, triethylsilyl, triisopropylsilyl and t-butyldimethylsilyl groups, diphenyl($C_1$-$C_4$)alkylsilyl groups such as a t-butyldiphenylsilyl group, di($C_1$-$C_4$)alkylphenylsilyl groups such as a dimethylphenylsilyl group, and a tribenzylsilyl group. Of these, the tri($C_1$-$C_4$)alkylsilyl groups, diphenyl($C_1$-$C_4$)alkylsilyl groups, and phenyl-di($C_1$-$C_4$)alkylsilyl groups are preferred, and t-butyldimethylsilyl and trimethylsilyl groups are especially preferred.

Examples of the group forming an acetal linkage together with the oxygen atom of the hydroxyl group include methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl and 6,6-dimethyl-3-oxa-2-oxobicyclo[3.1.0-]hex-4-yl groups. The 2-tetrahydropyranyl, 2-tetrahydrofuranyl, 1-ethoxyethyl, 2-ethoxy-2-propyl, (2-methoxyethoxy)methyl and 6,6-dimethyl-3-oxa-2-oxobicyclo[3.1.0]hex-4-yl groups are especially preferred. Above all, 2-tetrahydropyranyl is most preferred.

It should be understood that the silyl groups and the groups forming an acetal linkage are protective groups for the hydroxyl group. These protective groups can be easily removed under weakly acidic to neutral conditions in the stage of the final product to give a free hydroxyl group useful for drugs.

In formula [I], $R^4$ represents a hydrogen atom, a methyl group, and a vinyl group.

In formula [I], $R^5$ represents an unsubstituted linear or branched $C_3$-$C_8$ alkyl group which may be interrupted by an oxygen atom, a substituted linear or branched $C_1$-$C_5$ alkyl group in which the substituent is a $C_1$-$C_6$ alkoxy group or a phenyl, phenoxy or $C_3$-$C_{10}$ cycloalkyl group which may be substituted further, a phenyl group which may be substituted, a phenoxy group which may be substituted, or a $C_3$-$C_{10}$ cycloalkyl group which may be substituted.

Preferred examples of the unsubstituted linear or branched $C_3$-$C_8$ alkyl group which may be interrupted by an oxygen atom include propyl, butyl, pentyl, hexyl, heptyl, 2-hexyl, 2-methyl-2-hexyl, 2-methylbutyl, 2-methylpentyl, 2-methylhexyl and 2,2-dimethylhexyl.

Examples of the substituents in the substituted phenyl, phenoxy and $C_3$-$C_{10}$ cycloalkyl groups include halogen atoms, protected hydroxyl groups (such as silyloxy and $C_1$-$C_8$ alkoxy groups), and $C_1$-$C_4$ alkyl groups. Illustrative of the $C_3$-$C_{10}$ cycloalkyl groups are cyclopropyl, cyclopentyl, cyclohexyl, cyclohexenyl, cycloheptyl, cyclooctyl, and cyclodecyl groups. Of these, cyclopentyl and cyclohexyl groups are preferred.

In the linear or branched $C_1$-$C_5$ alkyl group substituted by a $C_1$-$C_6$ alkoxy or a phenyl, phenoxy or $C_3$-$C_{10}$ cycloalkyl which may be substituted, examples of the $C_1$-$C_6$ alkoxy group include methoxy, ethoxy, propoxy, isopropoxy, butoxy, t-butoxy and hexyloxy groups. The substituents of the phenyl, phenoxy or $C_3$-$C_{10}$ cycloalkyl group which may be substituted, and the $C_3$-$C_{10}$ cycloalkyl group may be the same as exemplified hereinabove. Examples of the linear or branched $C_1$-$C_5$ alkyl groups are methyl, ethyl, propyl, isopropyl, butyl, isobutyl, sec-butyl, t-butyl and pentyl groups. Preferred examples of $R^5$ are butyl, pentyl, hexyl, heptyl, 2-hexyl, 2-methyl-2-hexyl, 2-methylbutyl, 2-methylpentyl, cyclopentyl, cyclohexyl, phenyl, phenoxy, cyclopentylmethyl and cyclohexylmethyl groups. The substituents may be attached to arbitrary positions.

In formula [I], n represents 0 or 1, and Ar represents a substituted or unsubstituted phenyl group. Examples of the substituent for phenyl are phenyl and p-tolyl groups.

The compounds of formula [I] include stereoisomers since the bridgehead carbon atoms (1- and 5-positions) and the carbon atom which is substituted by $OR^2$ or ω-side chain (6- and 7-positions) of the bicyclo[3.3.0]octene ring, and the carbon atom which is substituted by $OR^3$ of ω-side chain are asymmetric. The compounds of this invention include any of these stereoisomers, and mixtures thereof in arbitrary ratios. Of these, compounds having a steric structure expressed by the formula are most preferred.

Specific preferred examples of the 3,6,7-trisubstituted bicyclo[3.3.0]-2-octenes of formula [I] provided by this invention are shown below.

(1) (1S, 5S, 6S, 7R)-3-(4-carbomethoxy-2,2-bisphenylsulfonylbutyl)-6-[(E, 3S)-3-hydroxy-1-octenyl]-7-hydroxybicyclo[3.3.0]-2-octene (2) (1S, 5S, 6S, 7R)-3-(4-carbomethoxy-2,2-bisphenylsulfonylbutyl)-6-[(E, 3S)-3-hydroxy-1-nonenyl]-7-hydroxybicyclo[3.3.0]-2-octene (3) (1S, 5S, 6S, 7R)-3-(4-carbomethoxy-2,2-bisphenylsulfonylbutyl)-6-[(E, 3S)-3-hydroxy-4-methyl-1-octenyl]-7-hydroxybicyclo[3.3.0]-2-octene (4) (1S, 5S, 6S, 7R)-3-(4-carbomethoxy-2,2-bisphenylsulfonylbutyl)-6-[(E, 3S)-3-hydroxy-4,4-dimethyl-1-octenyl]-7-hydroxybicyclo[3.3.0]-2-octene (5) 1S, 5S, 6S, 7R)-3-(4-carbomethoxy-2,2-bisphenylsulfonylbutyl)-6-[(E, 3S)-3-hydroxy-5-methyl-1-octenyl]-7-hydroxybicyclo[3.3.0]-2-octene (6) (1S, 5S, 6S, 7R)-3-(4-carbomethoxy-2,2-bisphenylsulfonylbutyl)-6-[(E, 3S)-3-hydroxy-5-methyl-1-nonenyl]-7-hydroxybicyclo[3.3.0]-2-octene (7) 6-[(E, 3S, 5S) . . . ] form of (6)

(8) 6-[(E, 3S, 5S) . . . ] form of (6)

(9) (1S, 5S, 6S, 7R)-3-(4-carbomethoxy-2,2-bisphenylsulfonylbutyl)-6-[(E, 3S)-3-hydroxy-3-cyclopentyl-1-propenyl]-7-hydroxybicyclo[3.3.0]-2-octene

(10) (1S, 5S, 6S, 7R)-3-(4-carbomethoxy-2,2-bisphenylsulfonylbutyl)-6-[(E, 3S)-3-hydroxy-3-cyclohexyl-1-propenyl]-7-hydroxybicyclo[3.3.0]-2-octene

(11) (1S, 5S, 6S, 7R)-3-(4-carbomethoxy-2,2-bisphenylsulfonylbutyl)-6-[(E, 3S)-3-hydroxy-3-cyclohexyl-1-butenyl]-7-hydroxybicyclo[3.3.0]-2-octene

(12) (1S, 5S, 6S, 7R)-3-(4-carbomethoxy-2,2-bisphenylsulfonylbutyl)-6-[(E, 3S)-3-hydroxy-5-phenoxy-1-pentenyl]-7-hydroxybicyclo[3.3.0]-2-octene

(13) (1S, 5S, 6S, 7R)-3-(4-carbomethoxy-2,2-bisphenylsulfonylbutyl)-6-[(E, 3S)-3-hydroxy-5-ethoxy-1-pentenyl]-7-hydroxybicyclo[3.3.0]-2-octene

(14) (1S, 5S, 6S, 7R)-3-(4-carbomethoxy-2,2-bisphenylsulfonylbutyl)-6-[(E, 4S)-4-hydroxy-4-methyl-1-octenyl]-7-hydroxybicyclo[3.3.0]-2-octene

(15) (1S, 5S, 6S, 7R)-3-(4-carbomethoxy-2,2-bisphenylsulfonylbutyl)-6-[(E, 4R)-4-hydroxy-4-methyl-1-octenyl]-7-hydroxybicyclo[3.3.0]-2-octene

(16) (1S, 5S, 6S, 7R)-3-(4-carbomethoxy-2,2-bisphenylsulfonylbutyl)-6-[(E)-4-hydroxy-4-vinyl-1-octenyl]-7-hydroxybicyclo[3.3.0]-2-octene

(17) (1S, 5S, 6S, 7R)-3-(4-carbomethoxy-2,2-bisphenylsulfonylbutyl)-6-[(E)-3-hydroxy-1-hept-7-en-1-yl]-7-hydroxybicyclo[3.3.0]-2-octene

(18) (1S, 5S, 6S, 7R)-3-(4-carbomethoxy-2,2-bisphenylsulfonylbutyl)-6-[(+)-3-hydroxy-1-oct-6-en-1-yl]-7-hydroxybicyclo[3.3.0]-2-octene

(19) 3-(4-carbomethoxy-1-p-trisulfonylbutyl) forms of (1) to (18)

(20) Compounds corresponding to (1) to (9) in which the methyl ester is a carboxylic acid

(21) Compounds corresponding to (1) to (9) in which the methyl ester changed to an allyl ester

(22) Compounds corresponding to (1) to (21) in which the hydroxyl group at the 7-position and the hydroxyl group on the substituent at the 6-position are protected with t-butyldimethylsilyl groups

(23) Compounds corresponding to (1) to (21) in which the hydroxyl groups on the substituents on the 7- and 6-positions are protected with 2-tetrahydropyranyl groups

(24) Enantiomorphs of compounds (1) to (23)

(25) Stereoisomers at the asymmetric carbons at which the hydroxyl groups on the substituents at the 1-, 5-, 6-, 7- and 6-positions of the compounds (1) to (23) are substituted The novel isocarbacyclins of formula [I] can be produced by treating a compound represented by the following formula [II]

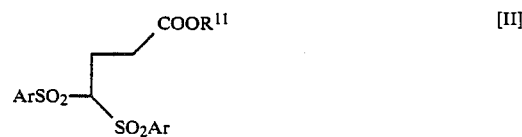

wherein $R^{11}$ represents a $C_1$-$C_4$ alkyl or alkenyl group, and Ar is as defined above, with a base, thereafter reacting the teated product regio-specifically with a 3,6,7-trisubstituted bicyclo[3.3.0]-2-octene which is a compound represented by the following formula [III-a]

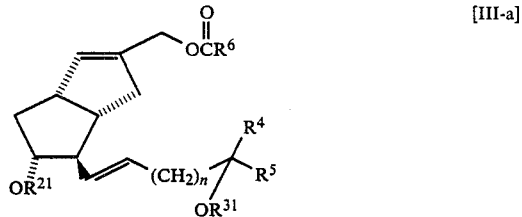

wherein $R^{21}$ and $R^{31}$ are identical or different and each represents a tri($C_1$-$C_7$)hydrocarbonsilyl group or a group forming an acetal linkage together with the oxygen atom of the hydroxyl group, $R^6$ represents a $C_1$-$C_6$ hydrocarbon group, and $R^4$, $R^5$ and n are as defined above, or its enantiomorph, or a mixture of both in an arbitrary ratio, in the presence of a palladium compound, and as required, subjecting the resulting product to a deprotection reaction or a hydrolysis reaction.

Likewise, the novel isocarbacyclins of formula [I] can be produced by treating a compound represented by the following formula [II]

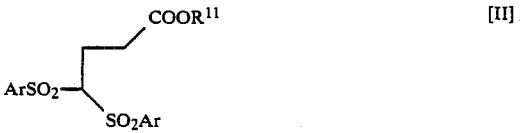

wherein $R^{11}$ and Ar are as defined above, with a base, thereafter reacting the teated product regio-specifically with a 3-methylene-2,6,7-trisubstituted bicyclo[3.3.0]-octene which is a compound represented by the following formula [IV-a]

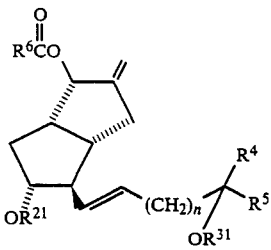

[IV-a]

wherein $R^{21}$, $R^{31}$, $R^4$, $R^5$, $R^6$ and n are as defined above, its enantiomorph, or a mixture of both in an arbitrary ratio, in the presence of a palladium compound, and as required, subjecting the resulting product to deprotecting reaction or hydrolysis reaction.

The isocarbacyclins of formula [I] can also be produced by reacting a 3,6,7-trisubstituted bicyclo[3.3.0]-2-octene which is a compound represented by the folowing formula [III-b]

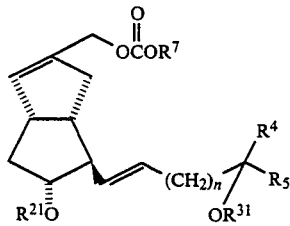

[III-b]

wherein $R^7$ represents a $C_1$–$C_4$ alkyl group, and $R^4$, $R^5$, $R^{21}$, $R^{31}$ and n are as defined above, its enantiomorph, or a mixture of both in an arbitrary ratio regio-specifically with a compound represented by the following formula [II]

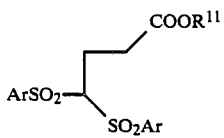

[II]

wherein Ar and $R^{11}$ are as defined above, in the presence of a palladium compound, and as required, subjecting the resulting product to deprotection reaction or hydrolysis reaction.

The isocarbocyclins of formula [I] can further be produced by reacting a 3-methylene-2,6,7-trisubstituted bicyclo[3.3.0]-octane which is a compound represented by the following formula [IV-b]

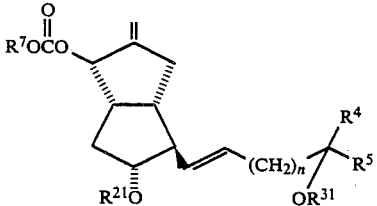

[IV-b]

wherein $R^4$, $R^5$, $R^7$, $R^{21}$, $R^{31}$ and n are as defined above, its enantiomorph or a mixture of both in an arbitrary ratio regio-specifically with a compounds of formula [II] given above in the presence of a palladium compound, and as required, subjecting the resulting product to deprotecting reaction and hydrolysis reaction.

In the starting bisarylsulfonyl compound of formula [II], $R^{11}$ represents an alkyl or alkenyl group having 1 to 4 carbon atoms. Preferred examples of such groups are the same as those given hereinabove with regard to $R^1$ in formula [I]. Especially preferably, $R^{11}$ is a methyl group.

In formula [II], Ar represents a substituted or unsubstituted phenyl group which may be the same as exemplified with regard to Ar in formula [I]. Ar preferably represents a phenyl or p-tolyl group.

In the allylacyloxy compound of formula [III-a] or [IV-a] and the carbonate compound of formula [III-b] or [IV-b], i.e. the other starting materials used in this invention, $R^{21}$ and $R^{31}$ are identical or different and each represents a tri($C_1$–$C_7$)hydrocarbon-silyl or a group forming an acetal linkage together with the oxygen atom of the hydroxyl group. Preferred examples of the tri($C_1$–$C_7$)hydrocarbon-silyl group and the acetal forming group for $R^{21}$ and $R^{31}$ may be the same as exemplified hereinabove with regard to $R^2$ and $R^3$ in formula [I].

In formulae [III-a], [IV-a], [III-b] and [IV-b], $R^4$ represents a hydrogen atom, a methyl group or a vinyl group. $R^5$ represents a linear or branched $C_3$–$C_9$ alkyl group which may be interrupted by an oxygen atom; a substituted or unsubstituted phenyl group; a substituted or unsubstituted phenoxy group; a substituted or unsubstituted $C_3$–$C_{10}$ cycloalkyl group; or a linear or branched $C_1$–$C_5$ alkyl group which is substituted by a $C_1$–$C_8$ alkoxy group, a phenyl group which may be substituted, or a $C_3$–$C_{10}$ cycloalkyl group which may be substituted. Preferred examples of $R^5$ may be those exemplified hereinabove with regard to $R^5$ in formula [I].

$R^6$ in formula [III-a] or [IV-a] represents a hydrocarbon group having 1 to 6 carbon atoms, and may includes methyl, ethyl, n-propyl, isopropyl, butyl and pentyl groups. The methyl group is preferred. $R^7$ in formula [III-b] or [IV-b] represents a hydrocarbon group having 1 to 4 carbon atoms, and may include, for example, a methyl, ethyl, n-propyl, isopropyl or butyl group. The methyl group is preferred.

The 3,6,7-trisubstituted-bicyclo[3.3.0]-2-octenes represented by formulae [III-a] and [III-b] are produced by a method identical with, or similar to, the method described in Shibasaki et al., Tetrahedron Letters, 25, 5087 (1984), which is schematically shown below in a simplified manner.

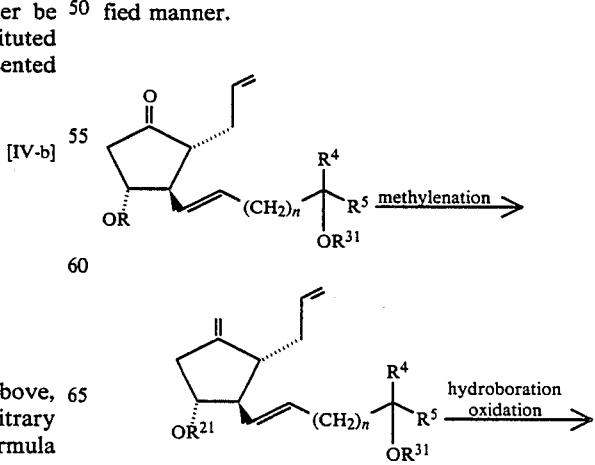

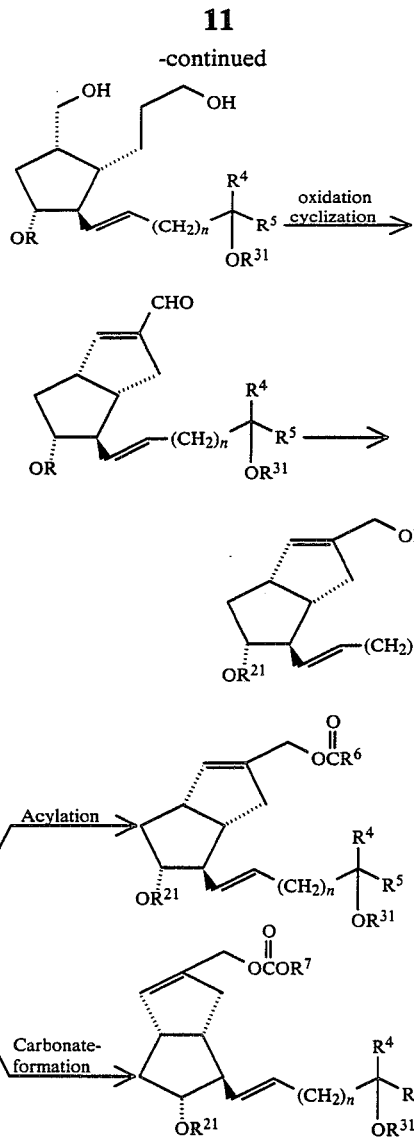

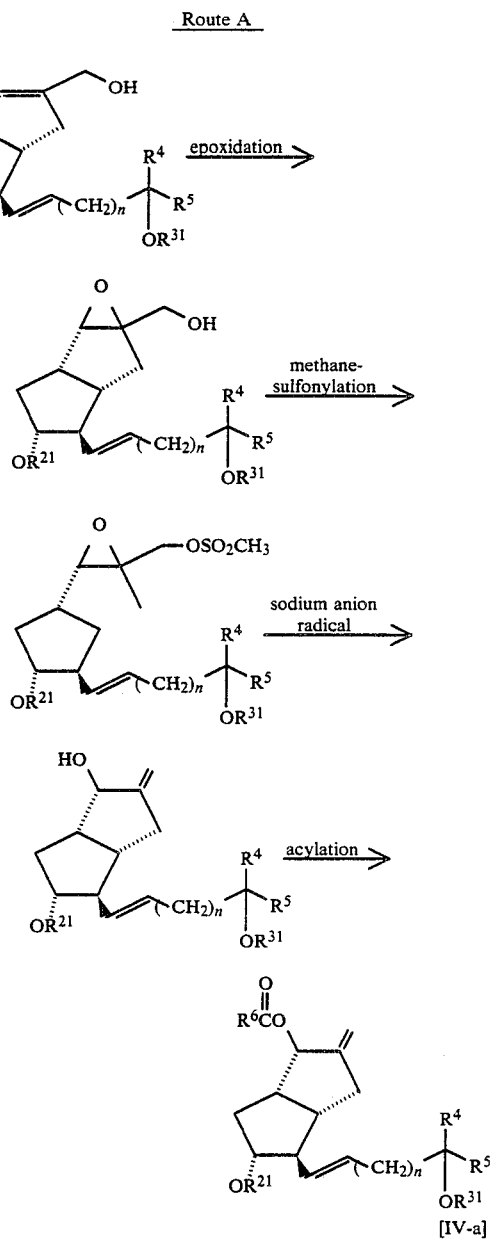

hydroxy-2-cyclopentenone shown in the present invention. These reaction routes are briefly shown below.

The 3-methylene-2,5,7-trisubstituted-bicyclo[3.3.0]-octanes represented by formulae [IV-a] and [IV-b] can be produced, for example, by a known synthesis route (route A shown below) from a 6,7-disubstituted-3-hydroxymethylbicyclo[3.3.0]-2-octene produced by the method described in the above-cited Tetrahedron Letters, 25, 5087 (1084) or a method similar to it. They can also be obtained by cyclization (route B) of an acetylene derivative obtained from the optically active 4-

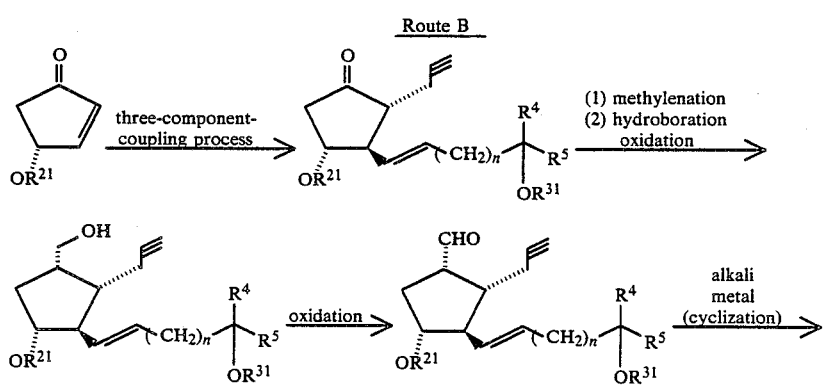

Route B

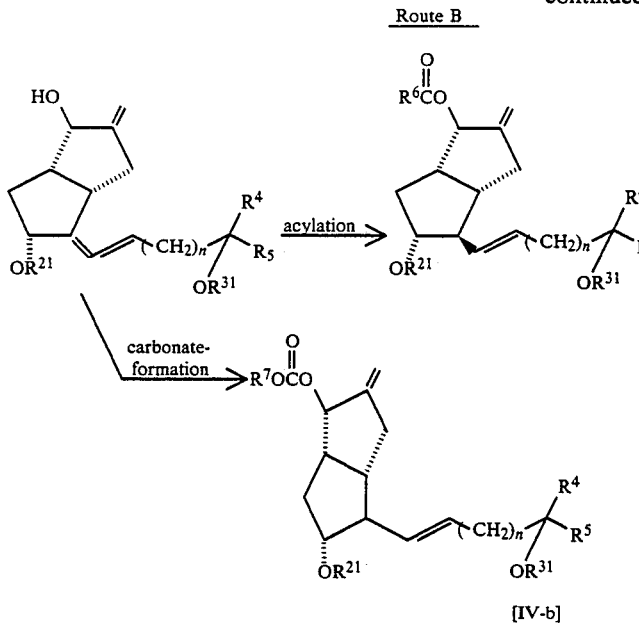

[IV-b]

The acylation reaction in the final step is carried out by reacting an acid chloride such as $R^6COCl$ where $R^6$ is as defined or an acid anhydride such as $(R^6CO)_2O$ with the allyl alcohol compound in the presence of a base. On the other hand, the reaction of forming a carbonate compound is carried out by reacting a chloroformate derivative such as $ClCOOR^7$ where $R^7$ is as defined above with the allyl alcohol compound in the presence of a base. Organic bases such as pyridine, triethylamine and diisopropylethylamine are preferably used as the base. As a result, the acyloxy compound of formula [III-a] or [IV-a] or the carbonate compound of formula [III-b] or [IV-b] can be obtained.

Synthesis of the 4,4-bisarylsulfonylisocarbacyclin of formula [I] from the acyloxy compound of formula [III-a] or [IV-a] is carried out by treating the bisarylsulfonyl compound of formula [II] with a base, and reacting the treated product with the acyloxy compound of formula [III-a] or [IV-a].

The bisaryl sulfonyl compound of formula [II] is used in an amount of 0.9 to 30 equivalents, preferably 1 to 5 equivalents, based on the acyloxy compound of formula [III-a] or [IV-a]. Examples of the base to treat the bisaryl sulfonyl compound include organic alkali metal compounds and alkali metal hydrides, such as n-butyllithium, sec-butyllithium, t-butyllithium, phenyllithium, methyllithium, naphthyllithium, tritylithium, lithium hydride, sodium hydroxide, potassium hydride, sodium methoxide and sodium ethoxide. Sodium hydride is preferred. The amount of the base is 0.5 to 30 equivalents, preferably 1 to 10 equivalents, per equivalent of the bisarylsulfonyl compound of formula [II]. In principle, the amount of the base is one equivalent. The temperature required for this salt-forming reaction is $-100°$ C. to $100°$ C., preferably $-78°$ C. to $2°$ C. The reaction time is 5 minutes to 50 hours, preferably 10 minutes to 2 hours. The reaction is carried out in an organic solvent, for example ethers such as diethyl ether, tetrahydrofuran and dioxane, hydrocarbons such as n-hexane and benzene, dimethylformamide (DMF) and dimethyl sulfoxide (DMSO). Tetrahydrofuran is preferably used.

The resulting reaction mixture can be reacted with the allylacyloxy compound of formula [III-a] or [IV-a] without isolating the alkali metal salt of the bisarylsulfonyl compound. This reaction is carried out in the presence of palladium. For example, the various palladium complexes described, for example, in Tetrahedron Letter, vol. 42, No. 16, pp. 4361–4401, 1986, Accounts of Chemical Research, vol. 13, No. 11, pp. 385–393, 1980, and J. Tsuji, "Organic Synthesis with Palladium Compounds", Springer-Verlag (1980). Especially preferably, tetrakis[triphenylphosphine)palladium(O), bis[bis(1,2-diphenylphosphino)ethane]palladium(O), or bis[bis(1,3-diphenylphosphino)propane]palladium(O) is used.

Synthesis of the 4,4-bisarylsulfonyl isocarbacyclins of formula [I] from the carbonate compound of formula [III-b] or [IV-b] is carried out by reacting the bisarylsulfonyl compound of formula [II] with the carbonate of formula [III-b] or [IV-b] in the presence of palladium. The bisarylsulfonyl compound of formula [II] is used in an amount of 0.5 to 30 equivalents, preferably 1 to 5 equivalents, per equivalent of the carbonate of formula [III-b] or [IV-b]. This reaction is carried out in the presence of a palladium complex. The palladium compound is preferably the one exemplified above. The amount of the palladium compound is 0.001 to 1 equivalent, preferably 0.01 to 0.2 equivalent, per equivalent of the carbonate of formula [III-b] or [IV-b]. The reaction temperature is $-30°$ C. to $200°$ C., preferably $0°$ to $100°$ C. The reaction time is 10 minutes to 100 hours, preferably 0.5 to 24 hours. As a reaction solvent, there may be used, for example, an ether such as diethyl ether, tetrahydrofuran or dioxane, a hydrocarbon solvent such as n-hexane or benzene, DMF and DMSO. Tetrahydrofuran is preferred.

The reaction carried out by using the carbonate of formula [III-b] or [IV-b] has the following advantages.

(1) Since decarboxylation reaction by Pd(O) takes place, the reaction proceeds irreversibly and mild reaction conditions can be used.

(2) An alkyloxy anion (for example, $MeO^\ominus$) occurs as a result of decarboxylation and extracts the hydrogens of methyl-4,4'-bisphenylsulfonyl butanoate to generate a compound of the following formula.

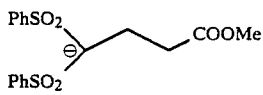

Hence, without adding a base (such as NaH) in advance to the reaction system, the reaction proceeds.

The resulting reaction mixture is worked up by methods usually practiced. For example, a difficultly water-soluble organic solvent such as hexane, pentane, diethyl ether or ethyl acetate is added to the reaction mixture. As required, the resulting mixture is washed with, for example, aqueous sodium chloride solution, followed by drying over a desiccant such as anhydrous magnesium sulfate or anhydrous sodium sulfate. Then, the organic solvent is removed under reduced pressure to obtain a crude product. As desired, the crude product can be purified by purifying means such as column chromatography, thin-layer chromatography or liquid chromatography.

When the resulting product is, as required, subjected to deprotection reaction and hydrolysis, the reaction proceeds regio-specifically, and the novel isocarbacyclin of formula [I] can be finally obtained. The protective group for the hydroxyl group can be carried out, for example, by treating the protected compound usually at a temperature of −78° C. to +30° C. using acetic acid, p-toluenesulfonic acid pyridinium salt or a cation exchange resin as a catalyst and water, tetrahydrofuran, diethyl ether, dioxane, acetone, acetonitrile, etc. as a reaction solvent, if the protective group forms an acetal linkage together with the oxygen atom of the hydroxyl group. If the protective group is a tri($C_1$-$C_7$)hydrocarbon-silyl group, it is removed by treating the protected compound in the same reaction solvent as above at the same temperature in the presence of, for example, acetic acid, tetrabutyl ammonium fluoride, cerium fluoride, aqueous hydrogen fluoride solution, or pyridine-hydrogen fluoride.

Hydrolysis of the ester is carried out by an ordinary method, namely by reacting it in water or a water-containing solvent together with lithium hydroxide, sodium hydroxide or potassium hydroxide at a temperature of −40° C. to +100° C., preferably 0° to 50° C., for 10 minutes to 24 hours.

As a result, the compound of formula [I] having an isocarbacyclin skeleton is produced.

Route B shown hereinabove as a process for producing the 3-methylene-2,6,7-trisubstituted-bicyclo[3.3.0]-octane of formula [IV-a] or [IV-b] is industrially important. The step of cyclizing the propargyl cyclopentane and subsequent steps in the process, which are especially important, will be described below in detail.

The propargylcyclopentane which is a compound represented by the following formula [V]

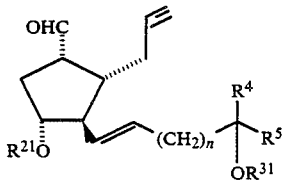

wherein $R^{21}$, $R^4$, $R^5$, $R^{31}$ and n are as defined above, its enantiomorph, or a mixture of both in an arbitrary ratio is cyclized with a reducing agent containing a metal species, and as required, deprotected to give a 6,7-disubstituted-2-hydroxy-3-methylenebicyclo[3.3.0]octane which is a compound represented by the following formula [VI]

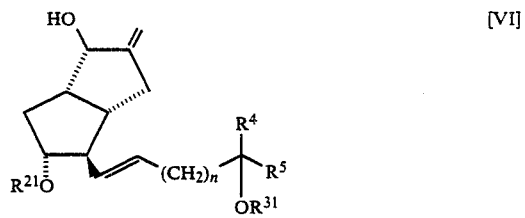

wherein $R^{21}$, $R^4$, $R^5$, $R^{31}$ and n are as defined above, its enantiomorph or a mixture of both in an arbitrary ratio.

The metal species of the reducing agent used in the cyclization reaction may, for example, be an alkali metal such as lithium, sodium and potassium. Sodium and lithium are especially preferred. It may also be an alkaline earth metal such as calcium and magnesium. The amount of the alkali metal or the alkaline earth metal used is 1.0 to 20.0 moles, preferably 1.2 to 10.0 moles, per mole of the propargyl cyclopentane of formula [V].

The reducing agent such as the alkali metal or the alkaline earth metal is used as an anion radical solution in the cyclization reaction. Suitable solvents for the anion radical solution include liquid ammonia and ether solvents such as diethyl ether, tetrahydrofuran and dimethoxyethane containing naphthalene, 1-(N,N-dimethylamino)-naphthalene or 4,4'-di-t-butylbiphenyl in an amount of at least 1 mole per mole of the alkali metal or the alkaline earth metal. Tetrahydrofuran containing naphthalene or 4,4'-di-t-butylbiphenyl is most preferred. The amount of the solvent may be one sufficient to make the reaction proceed smoothly. Usually, it is 1 to 100 times, preferably 2 to 20 times, the volume of the starting compound.

The reaction temperature is from −100° C. to +100° C., preferably −78° to +50° C., especially preferably −78° C. to 0° C. The reaction time varies depending upon the reaction temperature. Usually, the reaction ends within several hours at −78° to 0° C.

Zinc may also be used favorably as the metal species of the reducing agent. The cyclization using zinc is ordinarily carried out in the presence of trimethylchlorosilane and a base. The amount of zinc is 1 to 50 moles, preferably 10 to 30 moles, per mole of the propargyl cyclopentane of formula [V]. Zinc is activated prior to use with hydrochloric acid, copper, silver, mercury, etc. Trimethylchlorosilane is used in an amount of 1 to 20 moles, preferably 5 to 10 moles, per mole of the compound of formula [V]. The base is used in an amount of 1 to 10 moles, preferably 1 to 5 moles, per mole of the compound of formula [V].

The solvent for the cyclization reaction is preferably an ether solvent such as diethyl ether, tetrahydrofuran and dimethoxyethane. Tetrahydrofuran is most preferred. The amount of the solvent may be one sufficient to make the reaction proceed smoothly. Usually, it is 1 to 100 times, preferably 2 to 20 times, the volume of the starting compound.

The reaction temperature employed is 0° to 100° C., preferably 20° to 80° C. The reaction time varies depending upon the reaction temperature. Usually, the reaction ends within 30 minutes to 24 hours at a temperature of 20° to 80° C.

The resulting product can be taken out of the reaction system as a crude product by quenching, extraction, etc. using a saturated aqueous solution of ammonium chloride. As desired, the crude product can be purified by purifying means such as column chromatography, thin layer chromatography, liquid chromatography and recrystallization.

The product obtained by cyclization using zinc is a compound of the following formula

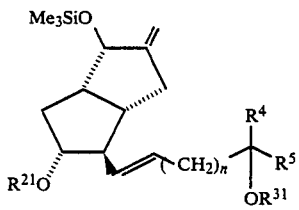

wherein $R^{21}$, $R^4$, $R^5$, $R^{31}$ and n are as defined above, its enantiomorph, or a mixture of both in an arbitrary ratio.

The trimethylsilyl ether at the 2-position of the resulting 6,7-disubstituted-3-methylene-2-trimethylsilyloxybicyclo[3.3.0]octane may be hydrolyzed to 2-hydroxyl by using an ordinary reagent for splitting off trimethylsilyl ether such as tetrabutyl ammonium fluoride (tetrahydrofuran as a solvent), p-toluenesulfonic acid (methanol as a solvent), potassium carbonate (methanol as solvent), citric acid, (methanol as a solvent), and p-toluenesulfonic acid/pyridine (methanol as a solvent). In other words, by carrying out the reaction in the same manner as the deprotecting reaction to be described below, the compound can be converted to the desired one. When a protected hydroxyl group exists at the 3'-position (or the 4'-position) of the 7- and 6-positions of the propargyl cyclopentane of formula [V] and the 6,7-disubstituted-2-hydroxy-3-methylenebicyclo[3.3.0]octane of formula [VI], it may be deprotected, as required, to form a free hydroxyl group.

If the protective group for the hydroxyl group is a group forming an acetal linkage together with the oxygen atom of the hydroxyl group, it may be eliminated conveniently by using acetic acid, a pyridinium salt of p-toluenesulfonic acid, a cation exchange resin, etc. as a catalyst and water, tetrahydrofuran, diethyl ether, dioxane, acetone, acetonitrile, etc. as a reaction solvent. The deprotecting reaction is carried out usually at −78° to +30° C. for about 10 minutes to 3 days. When the protective group is a tri($C_1$–$C_7$)hydrocarbon-silyl group, it can be eliminated by carrying out the reaction at the same temperature in the same reaction solvent as described above in the presence of acetic acid, tetrabutyl ammonium fluoride, cesium fluoride, hydrogen fluoride or pyridinehydrogen fluoride.

The compounds of formulae [V] and [VI] include stereoisomers since the carbon atom of the cyclopentane ring which is substituted by $OR^{21}$ of formyl or propargyl or ω-chain functional group (in the case of [V]), and the carbon atoms (1-, 2-, 5-, 6-, 7-positions of [VI]) of the bicyclo[3.3.0]octane ring, and the carbon atom which is substituted by $OR^{31}$ of ω-side chain are asymmetric. The compounds of this invention include any of these stereoisomers, and mixtures thereof in arbitrary ratios. Of these, compounds having a steric structure expressed by the formula are most preferred.

The processes of this invention for obtaining the isocarbacyclins of formula [I] have various advantages among which are:

(1) Starting materials which are easily available industrially can be used.

(2) Synthesis of the skeleton in accordance with the processes of the invention proceeds regiospecifically, and the yields of the products are high.

The novel isocarbacyclins of formula [I] are expected to have isocarbacyclin-like activities such as platelet aggregation inhibitory activity, vasodilating activity, antihypertensive activity and cell protecting activity, and are useful as intermediates for synthesis of isocarbacyclin which has a good prospect of use as a medicine.

The compound of formula [I], its enantiomorph or a mixture of the compound and its enantiomorph in an arbitrary ratio can be converted to a 9(O)-methanoprostacyclin which is a compound represented by the following formula [VII]

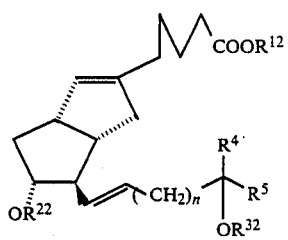

[VII]

wherein $R^{12}$ represents a hydrogen atom or a $C_1$–$C_4$ alkyl or alkenyl group, $R^{22}$ and $R^{32}$ are identical or different and each represents a hydrogen atom, a tri($C_1$–$C_7$)hydrocarbon-silyl group or a group forming an acetal linkage together with the oxygen atom of the hydroxyl group, and $R^4$, $R^5$ and n are as defined above, its enantiomorph or a mixture of both in an arbitrary ratio.

Specific examples of the $C_1$–$C_4$ alkyl or alkenyl group for $R^{12}$ may be the same as those exemplified with regard to $R^1$ in formula [I]. Specific examples of the hydroxy-protecting groups for $R^{22}$ and $R^{32}$ are also the same as those exemplified with regard to $R^2$ and $R^3$ in formula [I].

This desulfonation is carred out by reacting the compound of formula [I] with an alkali metal amalgam as a reducing agent. Basically, this reaction is carried out in accordance with the method of Trost et al., Tetrahedron Letters, 3477 (1976). Specifically, sodium amalgam is preferably used as the alkali metal amalgam, and sodium amalgam containing 1 to 20%, preferably 2 to 10%, of sodium is especially preferably used. The amount of the amalgam is used in an amount of 5 to 500 moles, preferably 50 to 500 moles, per mole of the 5-arylsulfonyl isocarbacyclin. The reaction temperature is −79° to +100° C., preferably −40° to +30° C. The reaction time varies depending upon the reaction temperature, and for example, a period of about 4 hours is sufficient at −10° C. This reaction is carried out in the presence of 1 to 10 moles, per mole of the compound of formula [I], of disodium phosphate.

The reaction is carried out in an organic solvent. Examples of the organic solvent are hexane, benzene, toluene, diethyl ether, tetrahydrofuran, dimethoxyethane, dioxane, N,N-dimethylformamide, methanol and ethanol. Methanol is preferred. The amount of the organic solvent may be one sufficient to make the reaction proceed smoothly. Usually, it is 1.0 to 100 times, preferably 5.0 to 50 times, the volume of the reactant.

The resulting reaction mixture may be worked up by ordinary methods. For example, a difficultly water-soluble organic solvent such as hexane, pentane, petroleum ether, diethyl ether and ethyl acetate is added to the reaction mixture. As required, the resulting mixture is washed with, for example, aqueous sodium chloride solution, and dried over a desiccant such as anhydrous magnesium sulfate, anhydrous sodium sulfate and anhydrous calcium chloride. The organic solvent is removed under reduced pressure to give a crude product. As desired, the crude product can be purified by purifying means such as column chromatography, thin layer chromatography and liquid chromatography.

The above desulfonation reaction may be carried out by a known method [cf. A. C. Brown et al., J. Org. Chem., 50, 1749 (1985)] using magnesium metal as the reducing agent insteacd of the alkali metal amalgam.

The resulting product may, as required, be subjected to deprotecting reaction and hydrolysis reaction to finally give an isocarbacyclin which is the compound of formula [VII], its enantiomorph or a mixture of both in an arbitrary ratio.

If the protective group for the hydroxyl group is a group forming an acetal linkage together with the oxygen atom of the hydroxyl group, it may be eliminated conveniently by using acetic acid, a pyridinium salt of p-toluenesulfonic acid, a cation exchange resin, etc. as a catalyst and water, tetrahydrofuran, diethyl ether, dioxane, acetone, acetonitrile, etc. as a reaction solvent. The deprotecting reaction is carried out usually at $-78°$ to $+30°$ C. for about 10 minutes to 3 days. When the protective group is a tri($C_1$-$C_7$)hydrocarbon-silyl group, it can be eliminated by carrying out the reaction at the same temperature in the same reaction solvent as described above in the presence of acetic acid, tetrabutyl ammonium fluoride, cesium fluoride, hydrogen fluoride or pyridinehydrogen fluoride.

As a result, the isocarbacyclins of formula [VII] which have a good prospect of utility as medicines can be obtained from the arylsulfonyl isocarbacyclins of formula [I] as starting materials.

The compounds of formula [V] can be produced from a 4-substituted-2-cyclopentenone as a starting material. A process for producing the compound of formula [V] is included within a process (to be described below as one embodiment of the invention) for producing a propargyl cyclopentane which is a compound represented by the following formula [VIII]

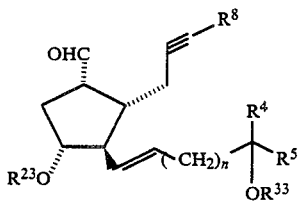

wherein $R^4$, $R^5$ and n are as defined above, $R^{23}$ and $R^{33}$ are identical or different and each represents a tri($C_1$-$C_7$)hydrocarbon-silyl group or a group forming an acetal linkage together with the oxygen atom of the hydroxyl group, $R^8$ represents a hydrogen atom or a $C_1$-$C_6$ saturated or unsaturated aliphatic hydrocarbon group which may be substituted by a ($C_1$-$C_6$alkyl)oxycarbonyl group or a hydroxyl group which may be protected, its enantiomorph or a mixture of both in an arbitrary ratio ([VIII] in which $R^8$ is a hydrogen atom corresponds to [V]).

As one embodiment, the present invention also provides a process for producing a propargylcyclopentane which is a compound represented by the following formula [VIII]

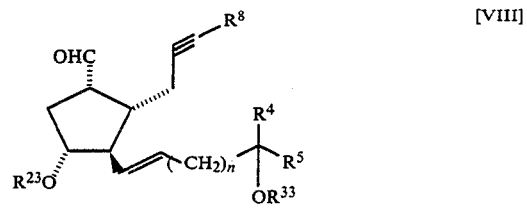

wherein $R^{23}$, $R^{33}$, $R^4$, $R^5$, $R^8$ and n are as defined above, which comprises subjecting a 4-substituted-2-cyclopentenone represented by the following formula [IX]

wherein $R^{24}$ represents a tri($C_1$-$C_7$)hydrocarbonsilyl group or a group forming an acetal linkage together with the oxygen atom of the hydroxyl group, to conjugation addition reaction with an organic copper compound formed from a vinyllithium represented by the following formula [X]

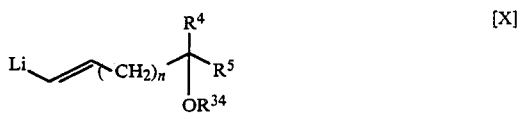

wherein $R^{34}$ represents a tri($C_1$-$C_7$)hydrocarbonsilyl group or a group forming an acetal linkage together with the oxygen atom of the hydroxyl group, and $R^4$, $R^5$ and n are as defined above, and a copper compound represented by the following formula [Xa]

wherein Q represents a halogen atom, a cyano group, a phenylthio group or a 1-pentynyl group, reacting the resulting enolate intermediate with a propargyl halide represented by the following formula [XI]

wherein $R^{81}$ represents a hydrogen atom, a trimethylsilyl group, or a $C_1$-$C_6$ saturated or unsaturated aliphatic hydrocarbon group which may be substituted by a ($C_1$-$C_6$ alkyl)oxycarbonyl group or a hydroxyl group which may be protected, and X repesents an iodine or bromine atom, in the presence of an organotin compound represented by the following formula (Xb)

$R_3SnY$ (Xb)

wherein three R's are identical or different and each represents a $C_1$-$C_4$ alkyl group, a $C_3$-$C_7$ cycloalkyl group or a halogen atom, Y represents a halogen atom or a trifurate group, provided that two or three R's are not simultaneously halogen atoms, to thereby form an alpha, beta, gamma-trisubstituted cyclopentanone represented by the following formula [XII]

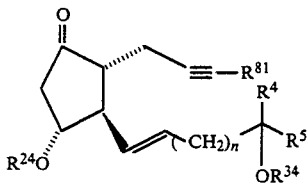
[XII]

wherein $R^{24}$, $R^{34}$, $R^4$, $R^5$, $R^{81}$ and n are as defined above, thereafter treating the trisubstituted cyclopentanone with a methylenation agent prepared from titanium tetrachloride, zinc and a dihalomethane to form an alpha, beta, gamma-trisubstituted methylenecyclopentane represented by the following formula [XIII]

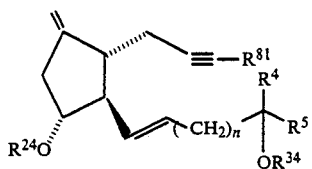
[XIII]

wherein $R^{24}$, $R^{34}$, $R^4$, $R^5$, $R^{81}$ and n are as defined above, hydroborating and subsequently oxidizing the trisubstituted methylenecyclopentane to form an alpha, beta, gamma-trisubstituted hydroxymethylcyclopentane represented by the following formula [XIV-a]

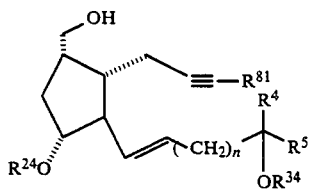
[XIV-a]

wherein $R^{24}$, $R^{34}$, $R^4$, $R^5$, $R^{81}$ and n are as defined hereinabove, subsequently, when $R^{81}$ is a trimetsilyl group, selectively deprotecting the tri-substitu hydroxymethylcyclopentane with sodium methoxide torm a compound of the following formula [XIV-b]

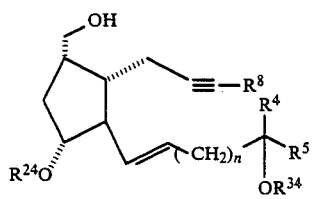
[XIV-b]

wherein $R^{24}$, $R^{34}$, $R^4$, $R^5$ and n are as defined above, $R^8$ repesents a $C_1$-$C_6$ saturated or unsaturated aliphatic hydrocarbon group which may be substituted by a ($C_1$-$C_6$ alkyl)oxycarbonyl group or a hydroxyl group which may be substituted, further oxidizing the resulting compound, and if required, subjecting it to deprotecting reaction.

As the compound of formula [V] corresponding to the compound of formula [VIII] in which $R^8$ represents a hydrogen atom is cyclized to form the compound of formula [VI], a compound of formula [VIII] in which $R^8$, $R^{23}$, and $R^{33}$ are not hydrogen atoms, for example a compound of the following formula [VIII']

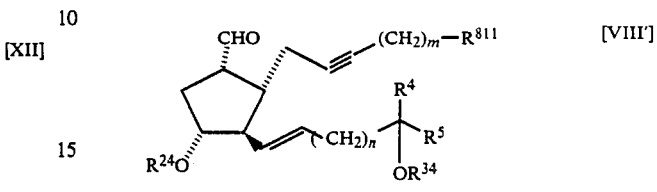
[VIII']

wherein $R^4$, $R^5$, $R^{24}$, $R^{34}$ and n are as defined above, $R^{811}$ represents a hydrogen atom or an aliphatic hydrocarbon group which may be substituted by a hydroxyl group which may be protected, and m is 0 or 1, can be cyclized under the same operating conditions as above to form a compound of the following formula [VIII'']

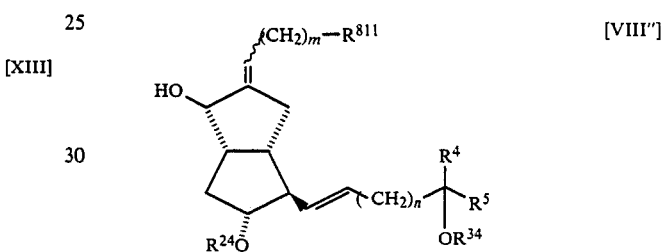
[VIII'']

wherein $R^4$, $R^5$, $R^{24}$, $R^{34}$, $R^{811}$, m and n are as defined above.

An isocarbacyclin which is a compound represented by the following formula [XIX]

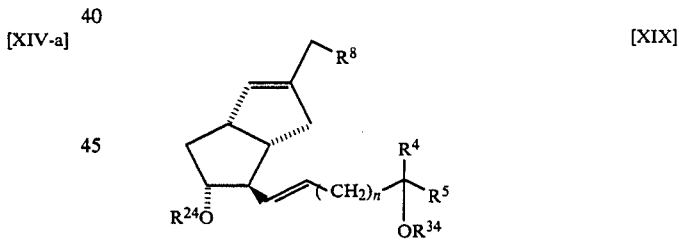
[XIX]

wherein $R^4$, $R^5$, $R^8$, $R^{24}$, $R^{34}$ and n are as defined above, its enantiomorph, or a mixture of both in an arbitrary ratio can be produced by reacting the compound of formula [VIII] with a lithium compound represented by the following formula [XVa] or [XVb]

$R^{41}R^{42}R^{43}SiLi$      XVa]

$(R^{41}R^{42}R^{43}Si)_q(L)_{2-q}CuLi$      [XVb]

wherein $R^{41}$, $R^{42}$ and $R^{43}$ are identical or different and each represents a $C_1$-$C_7$ hydrocarbon group, L represents a cyano, phenylthio or 1-pentynyl group, and q represents 1 ro 2, treating the product with carbon disulfide, reacting the treated compound with a halogen compound represented by the following formula [XVI]

$R^9X$      [XVI]

wherein $R^9$ represents a methyl or ethyl group, and X represents a halogen atom, to form a 9-substituted-5,6-dehydroPGE$_2$ which is a compound represented by the following formula [XVII]

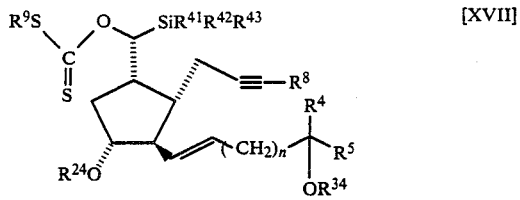

wherein $R^4$, $R^5$, $R^8$, $R^{41}$, $R^{42}$, $R^{43}$, $R^{24}$, $R^{34}$ and n are as defined above, its enantiomorph or a mixture of both in an arbitrary ratio, reacting this compound with tri-n-butyltin hydride in the presence of t-butyl peroxide to form a silylated carbacyclin which is a compound represented by the following formula [XVIII]

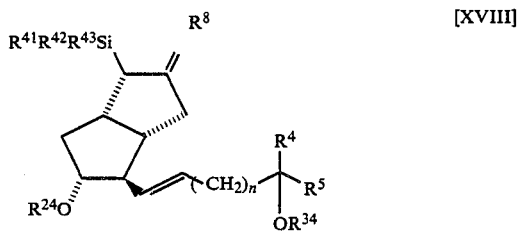

wherein $R^4$, $R^5$, $R^8$, $R^{11}$, $R^{24}$, $R^{34}$, $R^{41}$, $R^{42}$, $R^{43}$ and n are as defined above, and shows that the steric configuration of the double bond is E, Z or a mixture of E and Z, its enantiomorph or a mixture of both in an arbitrary ratio, treating the silylated carbacyclin with an acid, and if required, subjecting the treated compound to deprotecting reaction, hydrolysis reaction and/or salt-forming reaction.

The above process starts with the reaction of the compound of formula [VIII] with the lithium compound of formula [XVa] or [XVb] in an organic medium. In formula [XVa], $R^{41}$, $R^{42}$ and $R^{43}$ are identical or different and each represents a $C_1$-$C_7$ hydrocarbon group, such as methyl, ethyl, propyl, butyl, 1-butyl, phenyl and tolyl groups. The methyl, t-butyl and phenyl groups are especially preferred. Most preferred specific examples of the above lithium compound are dimethylphenylsilyl lithium and bis(dimethylphenyl)-copper lithium. The amount of the lithium compound used is 0.8 to 5 moles, preferably 0.9 to 3 moles, per mole of the compound of formula [VIII]. The organic medium for making the reaction proceed smoothly may be an organic medium inert to the lithium compound. Examples of the organic medium are ethers such as diethyl ether, tetrahydrofuran and dioxane, hydrocarbons such as pentane and hexane, and mixtures of these. Tetrahydrofuran is preferred. The reaction temperature is −100° to 0° C., preferably −78° to −40° C. Usually, a period of about 5 minutes to 30 minutes is sufficient as the reaction time. After the reaction, a polar medium such as hexamethylphosphoric triamide (HMPA) or 1,3-dimethyl-2-imidazoline (DMI) is added to the reaction mixture in an amount of about 1 to 20 moles, preferably 5 to 10 moles, per mole of the starting material [VIII] used. Then, carbon disulfide is added to the mixture. The amount of carbon disulfide used is 0.8 to 10 moles, preferably 0.9 to 6 moles. After the addition of carbon disulfide, the reaction temperature of the reaction mixture is raised, and the reaction is carried out at −10° to +10° C., preferably 0° to 5° C. A period of 30 minutes to 2 hours usually suffices as the reaction time. Then, the halogen compound of formula [XVI] is added to the reaction mixture, and the reaction is carried out to completion. In the halogen compound, the halogen atom X is, for example, an iodine or bromine atom. $R^9$ is, for example, a methyl or ethyl group. Methyl iodide is an especially preferred example of the halogen compound. The amount of the halogen compound used is 0.8 to 10 moles, preferably 0.9 to 6 moles, per mole of the starting material [VIII] used. The reaction temperature and time are the same as in the treatment with carbon dioxide. After the reaction, the reaction mixture is worked up in a customary manner. Specifically, the reaction mixture is mixed with a saturated aqueous solution of ammonium chloride or a saturated aqueous solution of ammonium sulfate and then with a difficultly water-soluble organic solvent such as hexane, pentane, petroleum ether, diethyl ether or ethyl acetate. As required, the resulting mixture is washed with, for example, an aqueous solution of sodium chloride, and dried over a desiccant such as anhydrous magnesium sulfate, anhydrous sodium sulfate or anhydrous calcium chloride. The organic medium is removed under reduced pressure to give a crude product. If desired, the crude product can be purified by purifying means such as column chromatography, thin-layer chromatography and liquid chromatography. As a result, the 9-substituted-5,6-dehydroPGE$_2$ represented by formula [XVII] is produced.

The reaction in the second step is cyclization involving treating the compound of formula [XVII] with tri-n-butyltin hydride and t-butyl peroxide. The amount of tri-n-butyltin hydride used is 50 to 0.8 mole, preferably 10 to 1 mole, per mole of the starting material [XVIII], and the amount of t-butyl peroxide used is 0.5 to 0.005 mole, preferably 0.1 to 0.01 mole, per mole of the starting material [XVII]. The reaction temperature is 0° to 120° C., preferably 50° to 100° C. The reaction time, which varies depending upon the reaction temperature, is usually about 40 hours at a reaction temperature of 70° C. An organic medium may be used in order to make the reaction proceed smoothly. Examples of the organic medium are aromatic hydrocarbons such as benzene and toluene, saturated hydrocarbons such as hexane, heptane and octanes, and mixtures thereof. Benzene is preferred. After the reaction, the reaction mixture is concentrated under reduced pressure. The crude reaction mixture is subjected to purifying means such as chromatography. Preferably, it is subjected to a purifying step after the peroxide which may possibly remain is decomposed with sodium thiosulfate, sodium sulfite, etc. As a result, the silylated carbacyclin of formula [XVIII] is produced.

The reaction in the third step is desilylation by treating the silylated carbacyclin of formula [XVIII] with an acid. Trifluoroacetic acid, acetic acid-boron trifluoride, sulfuric acid and hydriodic acid are examples of the acid used in desilylation. Trifluoroacetic acid is especially preferably used.

The amount of the acid used is 0.8 to 50 moles, preferably 1 to 30 moles, per mole of the silylated carbacyclin. The reaction temperature is 0° to 100° C., preferably 10° to 30° C. The reaction time varies depending upon the reaction temperature. Usually, a period of 10 minutes to 3 hours suffices. An organic medium may be used in order to make the reaction proceed smoothly.

Examples of the medium are halogenated hydrocarbons such as dichloromethane, dichlolroethane and chloroform. Dichloromethane is especially preferred. After the reaction, the reaction mixture is treated in a customary manner as in the first step described above. If required, the resulting product is subjected to deprotecting reaction, hydrolysis reaction and/or salt-forming reaction to give an isocarbacyclin which is a compound of the formula [XIX], its enantiomorph or a mixture of both in an arbitrary ratio.

According to this invention, the compound containing a carboxyl group formed by the hydrolysis reaction can, as required, be subjected to salt-forming reaction to give the corresponding carboxylate. The salt-forming reaction is known per se. The carboxylate can be formed by neutralizing the carboxylic acid compound by an ordinary method with a basic compound such as potassium hydroxide, sodium hydroxide or sodium carbonate, ammonia, trimethylamine, monoethanolamine, or morpholine in an amount nearly equal to the carboxylic acid compound.

According to the embodiment described above, the isocarbacyclin of formula [XIX] can be easily obtained by less process steps than in the prior art from the starting 9-deoxy-9-formyl-5,6-dehydroPGE$_2$ of formula [VIII] through a new intermediate by quite a new cyclizing method. The process in this embodiment, therefore, has a great industrial significance. The silylated carbacyclin of formula [XVIII], the intermediate, is a novel substance to the best of the knowledge of the present inventor. This compound is expected to have prostacyclin-like activities or lipoxygenase activity. The compound of formula [V] corresponding to the intermediate of formula [VIII] in which R$^8$ is a hydrogen atom is a novel intermediate for production of the novel carbacyclin or isocarbacyclin as described above.

The following Examples illustrate the present invention in greater detail. It should be understood however that the invention is not limited thereto. In the following examples, —OZ represents a t-butyldimethylsilyloxy group [—OSi.t—Bu.(CH$_3$)$_2$], and —OZ' represents a trimethylsilyloxy group [OSi(CH$_3$)$_3$].

EXAMPLE 1

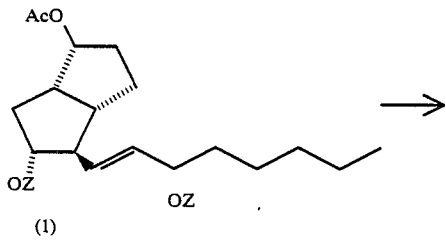

(1)

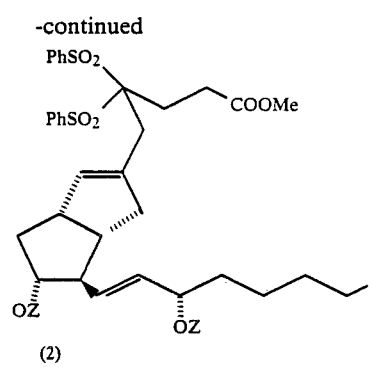

(2)

To a solution of 59 mg (1.05 mmole) of methyl-4,4-bis(phenylsulfonyl)butanoate in 0.8 ml of tetrahydrofuran (THF hereinafter) was added 6.2 mg (0.15 mmole) of NaH (60% in oil) in a stream of nitrogen, and the mixture was stirred for 1 hour. A solution of 68 mg (0.12 mmole) of an acetate compound represented by formula (1) above in 0.8 ml of THF was added, and then 6.3 mg (0.007 mmole) of bis[bis(1,2-diphenylphosphono)ethane]palladium (O) was added. The mixture was stirred at room temperature for 3 hours and then at 60° C. for 4 hours. After the reaction, a saturated aqueous solution of ammonium chloride was added to terminate the reaction. The reaction mixture was extracted with ethyl acetate. The organic layer was washed with water, saturated aqueous sodium chloride solution, dried over anhydrous magnesium sulfate, and concentrated under reduced pressure. The crude product was subjected to silica gel column chromatography (hexane/ethyl acetate=20:1→10:1) to give 64 mg (50%) of 4,4-bis(phenylsulfonyl)isocarbacyclin-11,15-bis(t-butyldimethylsilyl)ether methyl ester and 23 mg (34%) of the recovered acetate.

IR (cm$^{-1}$, neat): 2950, 2860, 1740, 1580, 1460, 1440, 1330, 1310, 1255, 1140.

NMR (δppm, CDCl$_3$): 0.9 (s+m, 21H), 1.2–2.4 (m, 14H), 2.6–3.1 (m, 7H), 3.7 (s, 3H), 3.75 (m, 1H), 4.05 (m, 1H), 5.4 (m, 2H), 5.55 (m, 1H), 7.1–8.0 (m, 10H).

EXAMPLE 2

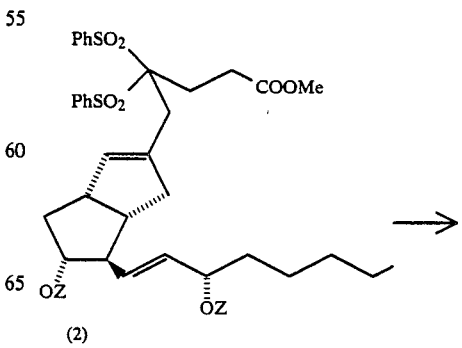

(2)

-continued

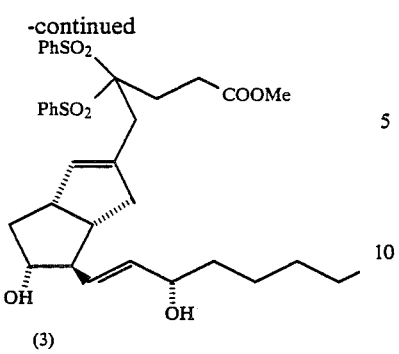
(3)

The disilyl compound (2) (87 mg; 0.10 mmole) was dissolved in 2 ml of dry THF, and 470 microliters (0.47 mmole) of a 1.0M THF solution of tetrabutyl ammonium fluoride was added, and the mixture was stirred at room temperature for 10 hours. Water was added, and the reaction mixture was extracted with ethyl acetate, and dried over anhydrous magnesium sulfate. The solvent was evaporated under reduced pressure. The residue was subjected to silica gel column chromatography (ethyl acetate, 2% methanol) to give 51 mg (79%) of the desilylated compound (3).

NMR (δppm, CDCl$_3$): 0.9 (m, 3H), 1.2–2.4 (m, 14H), 2.6–3.1 (m, 7H), 3.65 (s, 3H), 3.65–4.05 (m, 2H), 5.4 (m, 2H), 5.55 (m, 1H), 7.1–8.0 (m, 10H).

EXAMPLE 3

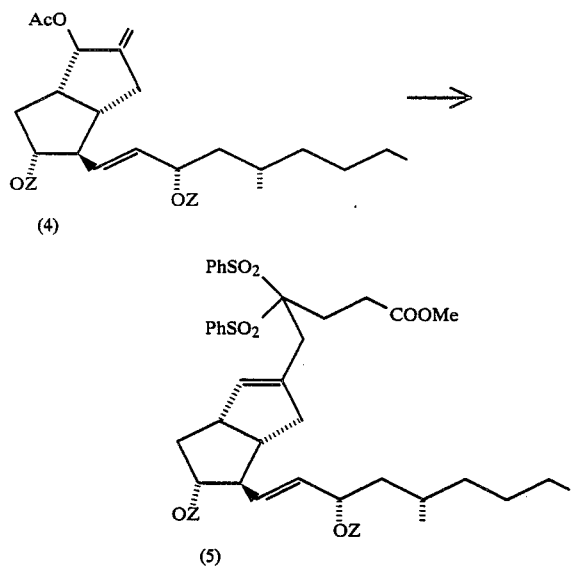

A solution of 116 mg (0.2 mmole) of the acetate of formula (4) above in 1 ml of THF was added to a solution of 94 mg (0.22 mmole) of methyl-4,4-bis(phenylsulfonyl)butanoate treated with 8.8 mg (60% in oil, 0.22 mmole) of NaH in a nitrogen stream in 1 ml of THF. Then, 13 mg (0.011 mmole) of tetrakis(triphenylphosphine)palladium (O) was added, and the mixture was stirred at 60° C. for 7 hours. After the reaction, a saturated aqueous solution of sodium chloride was added to terminate the reaction. The reaction mixture was extracted with ethyl acetate. The organic layer was washed with water and a saturated aqueous sodium chloride solution, dried over anhydrous magnesium sulfate, and concentrated under reduced pressure. The crude product was subjected to silica gel column chromatography (hexane:ethyl acetate = —20:1→10:1) to give 128 mg (71%) of 17(S),20-dimethyl-4,4-bis(phenylsulfonyl)isocarbacyclin disilyl ether methyl ester (5).

NMR (δppm, CDCl$_3$): 0.9 (s+m, 21H), 1.0–2.4 (m, 18H), 2.6–3.1 (m, 7H), 3.65 (s, 3H), 3.7–4.1 (m, 2H), 5.3–5.6 (m, 3H), 7.1–8.0 (m, 10H).

EXAMPLE 4

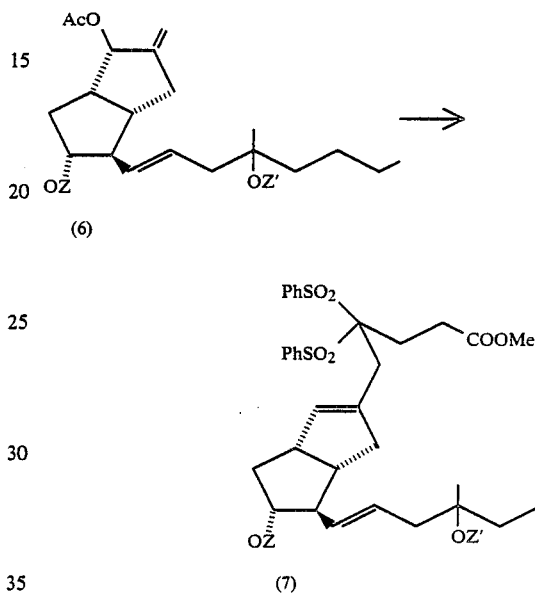

A solution of 78 mg (0.15 mmole) of the acetate of formula (6) above in 1 m of THF was added to a solution of 65 mg (0.17 mmole) of methyl-4,4-bis(phenylsulfonyl)butanoate treated with 6.8 mg (60% in oil, 0.17 mmole) of NaH in a nitrogen stream in 1 ml of THF. Then, 7.2 mg (0.008 mmole) of bis[bis(1,2-diphenylphosphino)ethane]palladium (O) was added, and the mixture was stirred at 80° C. Five hours after starting of stirring of the mixture, 7.2 mg (0.008 mmole) of the above palladium (O) compound was further added and the mixture was stirred for 5 hours. After the reaction, a saturated aqueous solution of ammonium chloride was added to terminate the reaction. The reaction mixture was extracted with ethyl acetate. The organic layer was washed with water and saturated aqueous sodium chloride solution, dried over anhydrous magnesium sulfate, and concentrated under reduced pressure. The crude product was subjected to silica gel column chromatography (n-hexane:ethyl acetate=20:1→10:1) to give 92 mg (78%) of the above product (7).

NMR (δppm CDCl$_3$): 0.9 (s+m, 12H), 1.1–2.4 (m, 14H), 1.1 (s, 3H), 2.6–3.1 (m, 7H), 3.65 (s, 3H), 3.8 (m, 1H), 5.3–5.6 (m, 3H), 7.1–8.0 (m, 10H).

EXAMPLE 5

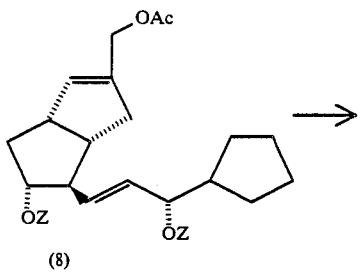
(8)

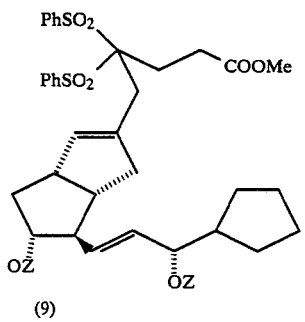
(9)

A solution of 110 mg (0.2 mmole) of the acetate compound representd by formula (8) above in 1 ml of DMF was added to a solution of 84 mg (0.22 mmole) of methyl-4,4-bis(phenylsulfonyl)butanoate treated with 9 mg (0.23 mmole, 60% in oil) of NaH in a nitrogen stream in 1 ml of THF, and then 9 mg (0.01 mmole) of bis[bis(1,2-diphenylphosphino)ethane]palladium (O) was added. The mixture was stirred at 60° C. for 5 hours. After the reaction, a saturated aqueous solution of ammonium chloride was added to terminate the reaction. The reaction mixture was extracted with ethyl acetate. The organic layer was washed with water and saturated aqueous sodium chloride solution, dried over anhydrous magnesium sulfate, and concentrated under reduced pressure. The crude product was subjected to silica gel column chromatography (n-hexane:ethyl acetate=20:1→10:1) to give 113 mg (65%) of the product of formula (9).

NMR (δppm CDCl$_3$): 0.9 (s, 18H), 1.0–2.4 (m, 15H), 2.6–3.0 (m, 7H), 3.70 (s, 3H), 3.6–4.1 (m, 2H), 5.3–5.6 (m, 3H), 7.1–8.0 (m, 10H).

EXAMPLE 6

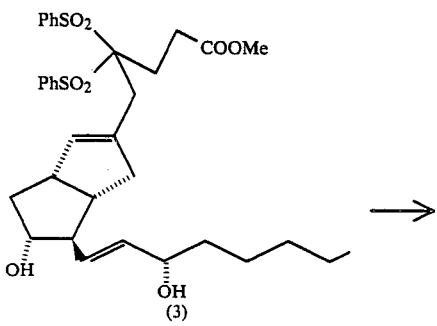
(3)

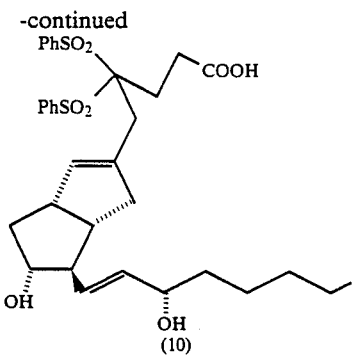
(10)

48 g (0.075 mmole) of 4,4-bis(phenylsulfonyl)isocarbacyclin methyl ester (3) was dissolved in a mixture of 3 ml of THF, 1.5 ml of methanol and 1 ml of water, and 60 mg of lithium hydroxide hydrate was added to the solution. The mixture was stirred at room temperature for 20 hours. Aqueous ammonium chloride solution was added, and the solvent was evaporated under reduced pressure. The residue was acidified with dilute hydrochloric acid to a pH of 3 to 4, and then extracted with ethyl acetate. The organic layer was washed with aqueous sodium chloride solution, dried over anhydrous magnesium sulfate, and concentrated. The crude product was purified by column chromatography (hexane:acetic acid=1:4) to give 40 mg (85%) of the carboxylic acid of formula (10).

NMR (δppm, CDCl$_3$): 0.9 (m, 3H), 1.2–2.4 (m, 14H), 2.6–3.1 (m, 7H), 3.6–4.1 (m, 2H), 5.4 (m, 2H), 5.6 (m, 1H), 7.1–8.0 (m, 10H).

EXAMPLE 7

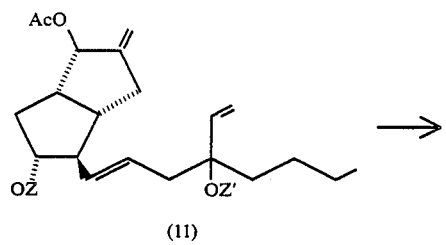
(11)

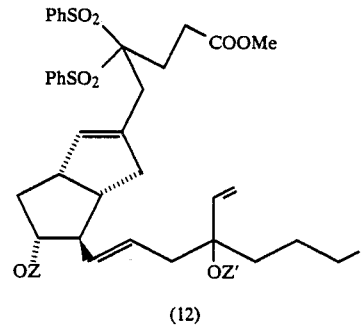
(12)

A solution of 70 mg (0.13 mmole) of the acetate compound represented by formula (11) in 0.8 ml of THF was added to a solution of 57 mg (0.15 mmole) of methyl-4,4-bis(phenylsulfonyl)butanoate treated with 6 mg of NaH (60% in oil, 0.15 mmole) in a nitrogen stream in 0.8 ml of THF, and then 6.3 mg (0.007 mmole) of bis[bis(1,2-diphenylphosphino)ethane]palladium (O) was added. The mixture was stirred at 70° C. for about 15 hours. After the reaction, saturated ammonium chloride solution was added to terminate the reaction. The reaction mixture was extracted with ethyl acetate, and the organic layer was washed with water and saturated aqueous sodium chloride solution, dried over anhydrous magnesium sulfate, and concentrated under reduced pressure. The crude product was subjected to silica gel column chromatography (n-hexane:ethyl acetate=20:1→5:1) to give 89 mg (79%) of the product (12).

NMR (δppm, CDCl₃): 0.9 (s+m, 12H), 1.1-2.4 (m, 14H), 2.6-3.1 (m, 7H), 3.65 (s, 3H), 3.8 (m, 1H), 4.7-5.6 (m, 6H), 7.1-8.0 (m, 10H).

EXAMPLE 8

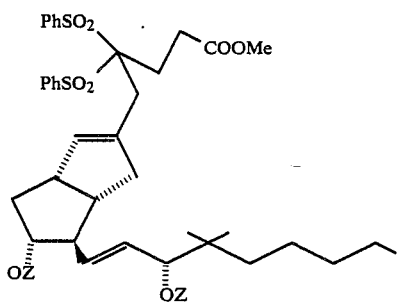

In the same way as in Example 7, the above compound was synthesized from the corresponding acetate and methyl-4,4-bis(phenylsulfonyl)butanoate.

Yield: 75%.

NMR (δppm, CDCl₃): 0.9 (s+m, 21H), 1.0-2.4 (m, 16H), 1.13 (s, 6H), 3.65 (s, 3H), 3.7-4.1 (m, 2H), 5.3-5.6 (m, 3H), 7.1-8.0 (m, 10H).

EXAMPLE 9

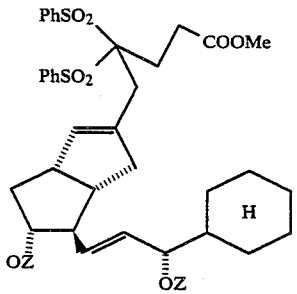

In the same way as in Example 7, the above compound was synthesized from the corresponding acetate and methyl-4,4-bis(phenylsulfonyl)butanoate.

Yield: 74%.

NMR (δppm, CDCl₃): 0.9 (s, 18H), 1.0-2.4 (m, 17H), 2.6-3.0 (m, 7H), 3.70 (s, 3H), 3.6-4.1 (m, 2H), 5.3-5.6 (m, 3H), 7.1-8.0 (m, 10H).

EXAMPLE 10

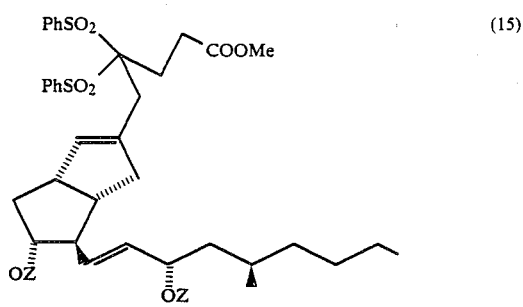

In the same way as in Example 7, the above compound was synthesized from the corresponding acetate and methyl-4,4-bis(phenylsulfonyl)butanoate.

Yield: 83%.

NMR (δppm, CDCl₃): 0.9 (s+m, 21H), 1.0-2.4 (m, 18H), 2.6-3.1 (m, 7H), 3.65 (s, 3H), 3.7-4.1 (m, 2H), 5.3-5.6 (m, 3H), 7.1-8.0 (m, 10H).

EXAMPLE 11

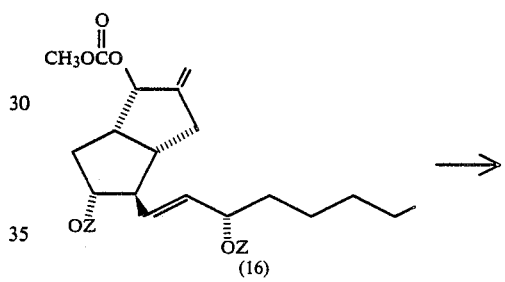

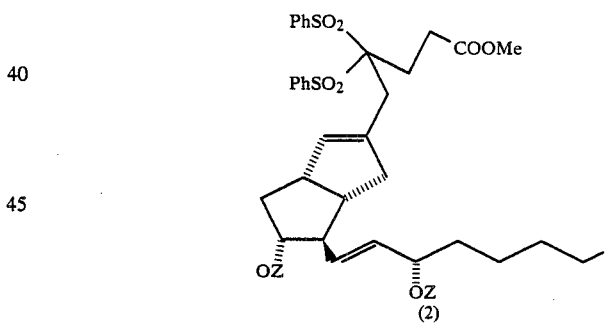

73 mg (0.13 mmole) of the methoxycarbonyloxy compound (16) and a solution of 57 mg (0.15 mmole) of methyl-4,4-bis(phenylsulfonyl)butanoate and 5.8 mg (0.0065 mmole) of bis[bis(1,2-diphenylphosphino)ethane]palladium (0) in 1 ml of THF were stirred at 50° C. for 4 hours in a stream of nitrogen. After the reaction, saturated aqueous ammonium chloride solution was added to terminate the reaction. The reaction mixture was extracted with ethyl acetate, and the organic layer was washed with water and saturated aqueous solution of sodium chloride, dried over anhydrous magnesium sulfate, and concentrated under reduced pressure. The crude product was subjected to silica gel column chromatography (hexane:ethyl acetate=20:1→10:1) to give 76 mg (68%) of 4,4-bis(phenylsulfonyl)isocarbacyclin-11,15-bis(t-butyldimethylsilyl)ether methyl ester (2).

IR (cm$^{-1}$, neat): 2950, 2860, 1740, 1580, 1460, 1440, 1330, 1310, 1255, 1140.

NMR (δppm, CDCl$_3$): 0.9 (s+m, 21H), 1.2–2.4 (m, 14H), 2.6–3.1 (m, 7H), 3.7 (s, 3H), 3.75 (m, 1H), 4.05 (m, 1H), 5.4 (m, 2H), 5.55 (m, 1H), 7.1–8.0 (m, 10H).

EXAMPLE 12

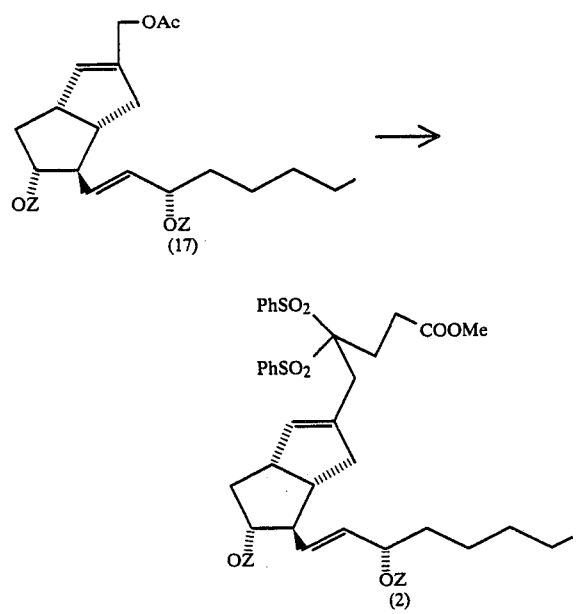

NaH [60% in oil; 44 mg (1.1 mmole)] was added at 0° C. to a solution of 400 mg (1.05 mmole) of methyl-4,4-bis(phenylsulfonyl)butanoate in 2 ml of THF in a stream of nitrogen. The mixture was stirred for 1 hour, and a solution of 450 mg (0.82 mmole) of the acetate of formula (17) in 2 ml of THF was added to the mixture. Furthermore, 80 mg (0.09 mmole) of bis[bis(1,2-diphenylphosphino)-ethane]palladium (O) was added, and the mixture was stirred at 60° C. for 5 hours. After the reaction, saturated aqueous ammonium chloride solution was added to terminate the reaction. The reaction mixture was extracted with ethyl acetate, and the organic layer was washed with saturated aqueous sodium chloride solution, dried over anhydrous magnesium sulfate, and concentrated under reduced pressure. The crude product was subjected to silica gel column chromatography (hexane:ethyl acetate=20:1→10:1) to give 493 mg (70%) of 4,4-bis(phenylsulfonyl)isocarbacyclin-11,15-bis(t-butyldimethylsilyl)ether methyl ester (2).

IR (cm$^{-1}$, neat): 2950, 2860, 1740, 1580, 1460, 1440, 1330, 1310, 1255, 1140.

NMR (δppm, CDCl$_3$): 0.9 (s+m, 21H), 1.2–2.4 (m, 14H), 2.6–3.1 (m, 7H), 3.7 (s, 3H), 3.75 (m, 1H), 4.05 (m, 1H), 5.4 (m, 2H), 5.55 (m, 1H), 7.1–8.0 (m, 10H).

EXAMPLE 13

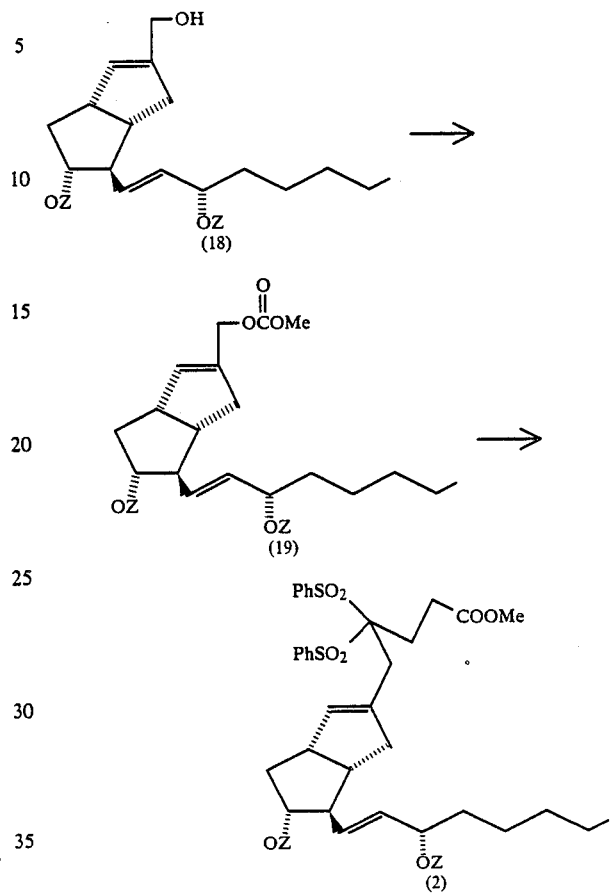

A solution of 225 mg (0.44 mmole) of the allyl alcohol represented by formula (18) above in 2 ml of methylene chloride was cooled to 0° C., and about 60 microliters (2 mmoles) of pyridine was added. Furthermore, 78 microliters (1 mmole) of methyl chloroformate was added, and the mixture was stirred for 1 hour. It was further stirred for 2 hours at room temperature.

The reaction was terminated with water, and the reaction mixture was extracted with diethyl ether. The organic layer was washed with aqeuous potassium hydrogen sulfate, saturated aqueous hydrogen carbonate solution and saturated aqueous sodium chloride solution in this order, and dried over anhydrous magnesium sulfate. The solvent was evaporated under reduced pressure, and the residue was subjected to silica gel column chromatography (hexane:ethyl acetate=20:1) to give 246 mg (98%) of the methoxycarbonyloxy compound of formula (19).

IR (cm$^{-1}$, neat): 2950, 2860, 1755, 1460, 1440, 1360, 1260, 1120.

NMR (δppm, CDCl$_3$): 0.85 (s, 9H), 0.9 (s, 9H), 0.8–1.0 (m, 3H), 1.0–1.8 (m, 8H), 1.8–2.5 (m, 6H), 3.0 (m, 1H), 3.8 (s, 3H), 3.7–4.2 (m, 2H), 4.7 (br. s, 2H), 5.5 (m, 2H), 5.7 (br. s, 1H).

Then, 340 mg (0.6 mmole) of the resulting methoxycarbonyloxy compound (19) and a solution of a mixture of 298 mg (0.78 mmole) of methyl-4,4-bis(phenylsulfonyl)butanoate and 45 mg (0.05 mmole) of bis[(1,2-diphenylphosphino)ethane]palladium (O) in 4 ml of THF were stirred at 60° C. for 6 hours. After the reaction, saturated aqueous solution of ammonium chloride was added to terminate the reaction. The reaction mixture was extracted with ethyl acetate, and the organic layer was washed with water and saturated aqeuous sodium chloride solution, dried over anhydrous magnesium sulfate, and concentrated under reduced pressure. The crude product was subjected to silica gel column chromatography (hexane:ethyl acetate=20:1→10:1) to give 157 mg (30%) of 4,4-bis(phenylsulfonyl)isocarbacyclin-11,15-bis(t-butyldimethylslyl)ether methyl ester (2).

IR (cm$^{-1}$, neat): 2950, 2860, 1740, 1580, 1460, 1440, 1330, 1310, 1255, 1140.

NMR (δppm, CDCl$_3$): 0.9 (s+m, 21H), 1.2-2.4 (m, 14H), 2.6-3.1 (m, 7H), 3.7 (s, 3H), 3.75 (m, 1H), 4.05 (m, 1H), 5.4 (m, 2H), 5.55 (m, 1H), 7.1-8.0 (m, 10H).

EXAMPLES 14-21

Example 13 was repeated except that each of the groups indicated in Table 1 was substituted for the dimethyl-t-butylsilyl group. Compounds of formula (I) in which R$^2$ and R$^3$ are as indicated in Table 1 were obtained.

TABLE 1

| Example | Group used instead of the dimethyl-t-butylsilyl group | R$^2$ and R$^3$ |
|---|---|---|
| 14 | tribenzylsilyl group | same as left |
| 15 | triethylsilyl group | same as left |
| 16 | t-butyldiphenylsilyl group | same as left |
| 17 | dimethylphenylsilyl group | same as left |
| 18 | methoxymethyl group | same as left |
| 19 | 1-ethoxyethyl group | same as left |
| 20 | 2-methoxy-2-propyl group | same as left |
| 21 | tetrahydropyranyl group | same as left |

EXAMPLE 22

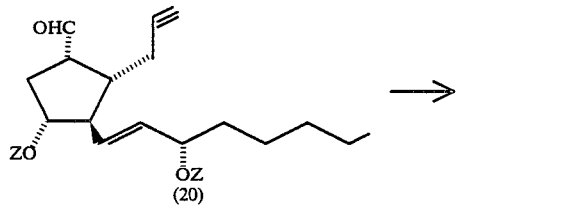
(20)

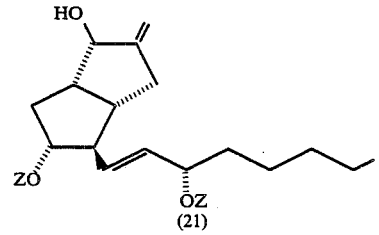
(21)

Metallic lithium (15 mg) and 266 mg of naphthalene were added to 7 ml of THF, and the mixture was stirred at room temperature for 2 hours to prepare a dark green anion radical solution. The solution was cooled to −50° C., and a solution of 50 mg of the compound (20) in 3 ml of THF was added. Five minutes later, saturated aqeuous ammonium chloride solution was added to quench the reaction mixture. The reaction mixture was extracted with ethyl acetate, and the organic layer was washed with saturated aqueous sodium chloride solution, dried over magnesium sulfate, and concentrated under reduced pressure to give 246 g of a crude product. The crude product was chromatographed on a silica gel column using a 9:1 mixture of hexane and ethyl acetate as an eluent to give 34 mg of the compound (21) in a yield of 67%.

The compound (21) consisted of 14 mg of the compound (21α) and 20 mg of the compound (21β) below.

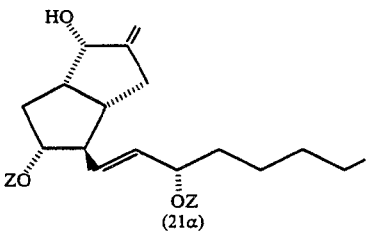
(21α)

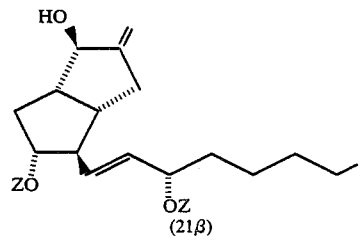
(21β)

NMR (δ$_{TMS}$$^{CDCl_3}$) for both (21α) and (21β) 0.8-1.0 (21H, m), 3.5-4.2 (4H, br), 4.91 (1H, brs), 5.01 (1H, brs), 5.43 (2H, m).

Rf (silica gel thin layer chromatography; developing solvent: n-hexane/ethyl acetate=4/1): (21α): 0.43, (21β): 0.30.

EXAMPLE 23

Metallic lithium (15 mg), 553 mg of 4,4'-di-t-butyl-biphenyl and 5 ml of THF were stirred at 0° C. for 18 hours to prepare a dark green anion radical solution. The solution was cooled to −50° C., and a solution of 50.6 mg of the compound (20) in 3 ml of THF was added. Five minutes later, the reaction mixture was quenched, and then worked up as in Example 22 to give 30 mg of the compound (21) [(11 mg of (21α) and 19 mg of (21β)]. The yield of compound (21) was 59%.

EXAMPLE 24

Metallic sodium (14 mg), 85 mg of naphthalene and 2 ml of THF were stirred at room temperature for 2.5 hours to prepare an anion radical solution. The solution was cooled to −70° C., and a solution of 51 mg of the compound (20) in 1.2 ml of THF was added. The mixture was stirred at −70° C. for 1 hour, and the reaction mixture was quenched with saturated aqueous ammonium chloride solution and worked up as in Example 22 to give 25 mg of the compound (21) [7 mg of (21α) and 18 mg of (21β)]. The yield of the compound (21) was 42%.

EXAMPLE 25

A flask holding 28 mg of metallic sodium was cooled to −70° C. in a nitrogen atmosphere, and about 7 ml of liquid ammonia was taken into the flask, and the mixture in the flask was concentrated with stirring. A solution of 51 mg of the compound (20) in 3.5 ml of THF was added at −45° C., and the mixture was stirred for 50 minutes. Then, 432 mg of sodium benzoate was added, and the mixture was stirred for 20 minutes to gasify ammonia. Water was added, and the reaction mixture was extracted twice with diethyl ether. The organic layer was washed with saturated aqueous solution of sodium hydrogen carbonate, saturated aqueous ammonium chloride solution and aqueous sodium chloride solution in this order, dried over anhydrous magnesium sulfate, and concentrated under reduced pressure to give 48 mg of a crude product. The crude product was chromatographed on a column of silica gel using a mixture of n-hexane and ethyl acetate in a ratio of 87.5:2.5 to give 10 mg of the compound (21) [only (21β)]. Yield: 20%.

EXAMPLE 26

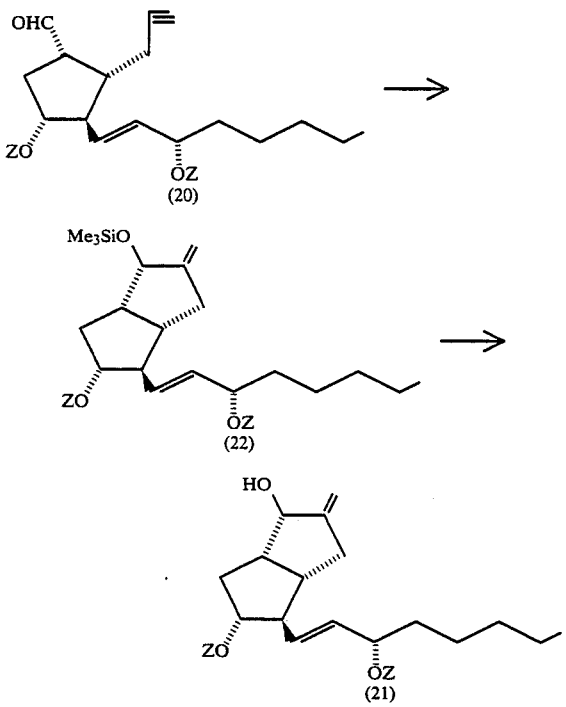

Zinc dust was stirred for 5 minutes in 10% hydrochloric acid. The supernatant was removed by decantation, and the residue was washed once with water, three times with acetone and twice with diethyl ether, and then dried in vacuum for 2 hours to activate it. To 53 mg of the compound (20) was added 138 mg of this zinc dust, and further, a solution of 68 mg of trimethylchlorosilane in 1 ml of THF was added. Furthermore, 32 mg of 2,6-lutidine was added, and the mixture was refluxed for 4 hours. The reaction mixture was separated into a solid and a liquid by decantation. Ten milliliters of diethyl ether was added to the liquid, and the organic layer was washed with saturated aqueous potassium hydrogensulfate solution, saturated aqueous sodium chloride solution and aqueous sodium chloride solution in this order, dried over anhydrous magnesium sulfate, and concentrated under reduced pressure. The resulting crude product containing the compound (22) was dissolved in 3 ml of methanol, and a small amount of pyridinium p-toluenesulfonate was added. The mixture was stirred at room temperature for 10 minutes. Saturated aqueous sodium bicarbonate solution was added, and the mixture was concentrated under reduced pressure to evaporate methanol. The residue was extracted with diethyl ether, and the organic layer was washed with aqueous sodium chloride solution, dried over anhydrous magnesium sulfate, and concentrated under reduced pressure. The crude product was subjected to silica gel column chromatography using a 19:1 mixture of n-hexane and ethyl acetate as an eluent to give 11.g mg of the compound (21) in a yield of 23%.

EXAMPLE 27

Zinc dust was stirred for 1 minute in 3% hydrochloric acid, and this washing was repeated four times. It was further washed five times with distilled water, twice with 2% aqueous copper sulfate solution, further 5 times with distilled water, four times with anhydrous ethanol, and five times with diethyl ether. The product was filtered by a glass filter in a stream of nitrogen gas, and dried under reduced pressure for 4 hours to activate it.

To 53 mg of the compound (20) were added 138 mg of the activated zinc dust, a solution of 68 mg of trimethylchlorosilane in 1 ml of THF, and the mixture was refluxed for 4 hours.

The reaction mixture was worked up, desilylated and purified as in Example 26 to give 16 mg (yield 31%) of the compound (21).

EXAMPLE 28

Zinc dust (350 mg) was stirred in 10% hydrochloric acid for 4 minutes, and the supernatant was removed by decantation. The residue was washed with acetone and then with diethyl ether, and a suspension of 12 mg of silver acetate in 1.7 ml of boiling acetic acid was added, and the mixture was stirred for 1 minute. The supernatant was removed by a syringe, and the product was washed with 1 ml of acetic acid, three times with 2 ml of diethyl ether, 2 ml of methanol, further four times with 2 ml of diethyl ether and 4 times with 2 ml of THF, and dried in vacuum for 3 hours to activate it.

To 53 mg of the compound (20) were added 138 mg of the activated zinc dust, a solution of 68 mg of trimethylchlorosilane in 1 ml of THF, and 32 mg of 2,6-lutidine, and the mixture was refluxed for 4 hours. The reaction mixture was worked up, desilylated and purified as in Example 26 to give 18 mg of the compound (21). Yield 34%.

EXAMPLE 29

Zinc dust (4.12 g) was stirred for 2 minutes in 10% hydrochloric acid, and the supernatant was removed by decantation. The residue was washed four times with 5 ml of distilled water, and a solution of 0.8 g of mercuric chloride in 5 ml of boiling water was added. The mixture was stirred for 10 minutes. After removing the supernatant, the residue was washed with 5 ml of distilled water, 7 times with 5 ml of ethanol, and further seven times with 5 ml of diethyl ether in this sequence, and then dried in vacuum for 3 hours to prepare activated zinc dust.

To 53 mg of the compound (20) were added 138 mg of the activated zinc dust, a solution of 68 mg of trimethylchlorosilane in 1 ml of THF and 32 mg of 2,6-lutidine, and the mixture was refluxed for 4 hours. The reaction mixture was worked up, desilylated and purified as in Example 26 to give 17 mg of the compound (21). Yield 32%.

EXAMPLE 30

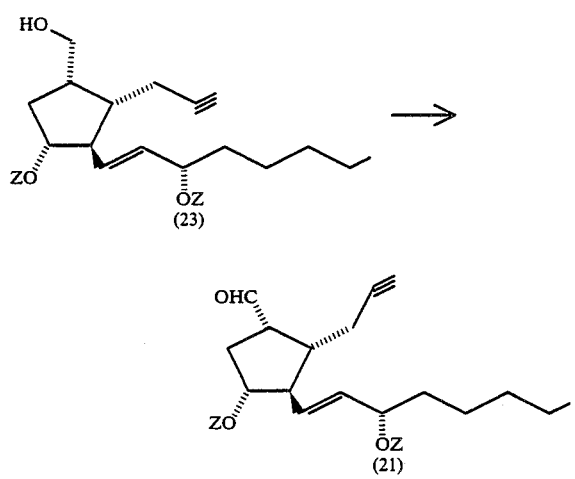

Pyridine (5.05 ml) was dissolved in 50 ml of methylene chloride, and 3.12 g of chromium trioxide was added. The mixture was stirred at room temperature for 20 minutes. A solution of 1.30 g of the compound (23) in 3 ml of methylene chloride was added, and the mixture was stirred at room temperature for 15 minutes. Diethyl ether (150 ml) was added, and the mixture was suction-filtered thorugh Celite to remove the solid. The organic layer was washed with saturated aqueous potassium hydrogensulfate and twice with aqueous sodium chloride solution, and dried over anhydrous magnesium sulfate. The solvent was removed under reduced pressure to give 1.32 g of a crude product. The crude product was purified by silica gel column chromatography. Eluates obtained with n-hexane/ethyl acetate (19/1) contained 1.01 g of the compound (21). Yield 77%.

NMR spectal data of the product were as follows: $\delta_{TMS}^{CDCl_3}$: ppm; 0.88 (21H), 2.87 (1H, m), 3.7–4.3 (2H, m), 5.43 (2H, m), 9.97 (1H, d, J=3 HZ).

EXAMPLE 31

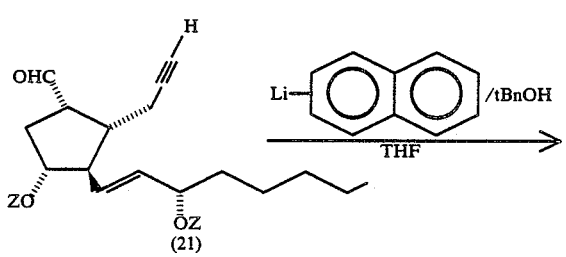

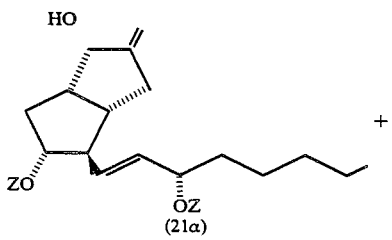

+

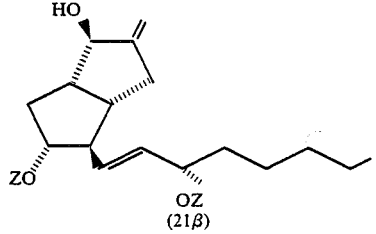

THF (550 ml) was added to 15.3 g (552 mmoles) of a mineral oil dispersion of lithium (content 25%, containing 1% sodium), and under ice cooling, 70.3 g (550 mmoles) of naphthalene was added in an atmosphere of nitrogen. Under ice cooling, the mixture was stirred for 2 hours to prepare a dark green anion radical solution. 25.1 g (50 mmoles) of acetylene aldehyde (21) and 18.7 ml (320 moles) of t-butanol were dissolved in 120 ml of THF, and the solution was cooled to −70° C. The above anion radical solution cooled at −70° C. was added. The mixture was stirred at −70° C. for 15 minutes, and 50 g of ammonium chloride was added. Furthermore, ethanol was added until the dark green color of anion radical disappeared. Saturated aqueous ammonium chloride solution (900 ml) was added, and the mixture was extracted twice with 700 ml of ethyl acetate. The organic layers were combined, washed twice with saturated aqueous sodium chloride solution, and dried over anhydrous magnesium sulfate. The solvent was evaporated under reduced pressure. The resulting crude product was purified by silica gel column chromatography to give 5.34 g (yield 21%) of the compound (21α) in eluates obtained with hexane/ethyl acetate (19/1) and 12.95 g (yield 51%) of the compound (21β) in eluates obtained with hexane/ethyl cetate (9/1).

Spectral data of the products were as follows: [21α] NMR ($\delta_{TMS}^{CDCl_3}$): 0.8–1.0 (21H), 3.86 (1H, q, S=6 Hz), 4.05 (1H, br), 4.38 (1H, bt, J=8 Hz), 4.96 (1H, brs), 5.08 (1H, brs), 5.45 (2H, m).

IR (cm$^{-1}$, liquid film): 3350, 3080, 1662, 1255, 1115, 1002, 968, 935, 835, 772.

MS 508 (M+), 491 (M-17), 451 (M-57). [21β] NMR ($\delta_{TMS}^{CDCl_3}$): 0.8–1.0 (21H), 3.77 (1H, m), 4.05 (1H, br), 4.15 (1H, brs), 4.95 (1H, brs), 5.07 (1H, brs), 5.46 (2H, m).

IR (cm$^{-1}$, liquid film): 3350, 3080, 1662, 1255, 1115, 1002, 968, 937, 835, 772.

MS 508 (M+), 491 (M-17), 451 (M-57).

EXAMPLE 32

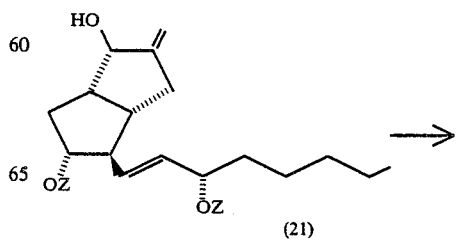

-continued

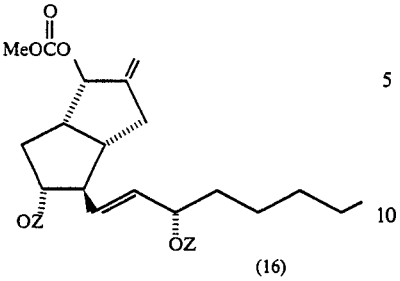

(16)

Pyridine (about 250 microliters; about 4 equivalents) was added at −20° C. in a stream of nitrogen to a methylene chloride solution (4 ml) of 400 mg (0.79 mmole) of (1S,5S,6S,7R)-2-hydroxy-3-methylene-6-[(E,3S)-3-t-butyldimethylsilyloxy-1-octenyl]-7-t-butyldimethyl-silyloxybicyclo[3.3.0]octane (21), and then 122 microliters (1.6 mmole) of methyl chloroformate was added. The mixture was stirred for 1 hour. Then, it was further stirred for 30 minutes at 0° C. Water was added to terminate the reaction, and the reaction mixture was extracted with ethyl acetate. The organic layer was washed with aqueous potassium hydrogensulfate solution, saturated aqueous sodium hydrogen carbonate solution and saturated aqueous sodium chloride solution in this order, and dried over anhydrous magnesium sulfate. Under reduced pressure, the solvent was evaporated, and the residue was subjected to silica gel column chromatography (hexane/ethyl acetate=15/1) to give 377 mg (85%) of the 2-methylcarbonyldioxy compound (16).

IR (cm$^{-1}$, neat): 2950, 2860, 1750, 1460, 1440, 1360, 1260, 1120.

NMR (δppm, CDCl$_3$): 0.85 (s, 9H), 0.87 (s, 9H), 0.8–2.6 (m, 18H), 3.75 (m, 1H), 3.8 (s, 3H), 4.07 (m, 1H), 5.0 (s, 1H), 5.15 (s, 1H), 5.3 (s, 1H), 5.5 (m, 2H).

EXAMPLE 33

In accordance with Example 31, compounds having different $$-\!\!\!\!+\!CH_2\!\!\xrightarrow{}_n\!\!-\!\!\!\underset{OR^{31}}{\overset{R^4}{|}}\!\!-R^5$$

moieties in formula [VI] were syntehsized as shown in the following table.

| Run No. | $-\!\!+\!CH_2\!\!\xrightarrow{}_n\!\!-\!\!\underset{OR^{31}}{\overset{R^4}{|}}\!\!-R^5$ | Yield NMR(δppm, CDCl$_3$) |
|---|---|---|
| 1 | 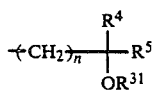 | Yield (αβ mixture): 75% NMR(δppm, CDCl$_3$); 0.8–1.0(21H, m), 3.5–4.2 (4H, m), 4.9(1H, brs), 5.1(1H, brs), 5.45(2H, m) |
| 2 | | Yield (αβ mixture): 70% 0.8–1.0(21H, m), 3.5–4.2 (4H, m), 4.9(1H, brs), 5.1(1H, brs), 5.45(2H, m) |
| 3 | | Yield (αβ mixture): 68% 0.9–1.0(21H, m), 3.3–4.2 (4H, m), 4.8(1H, brs), 5.1(1H, brs), 5.43(2H, m) |
| 4 | | Yield (αβ mixture): 74% 0.9–1.0(21H, m), 3.4–4.2 (4H, m), 4.9(1H, brs), 5.1(1H, brs), 5.45(2H, m) |
| 5 | | Yield (αβ mixture): 63% 0.9–1.0(21H, m), 1.13(6H, s), 3.4–4.2(4H, m), 4.9(1H, brs), 5.1(1H, brs), 5.45(2H, m) |
| 6 | | Yield (αβ mixture): 70% 0.9–1.0(12H, m), 1.1(3H, s), 3.4–4.1(4H, m), 4.85(1H, brs), 5.1(1H, brs), 5.45(2H, m) |
| 7 | | Yield (αβ mixture): 65% 0.9–1.0(12H, m), 3.4–4.2(4H, m), 4.7–5.6(7H, m) |

EXAMPLE 34

In accordance with Example 32, compounds having different $$-\!\!\!\!+\!CH_2\!\!\xrightarrow{}_n\!\!-\!\!\!\underset{OR^{31}}{\overset{R^4}{|}}\!\!-R^5$$

moieties in formula [IV-b] were synthesized as shown in the following table.

| Run No. | $-\!\!+\!CH_2\!\!\xrightarrow{}_n\!\!-\!\!\underset{OR^{31}}{\overset{R^4}{|}}\!\!-R^5$ | Yield NMR (δ ppm, CDCl$_3$) |
|---|---|---|
| 1 | 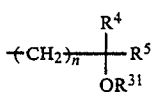 | Yield: 90% NMR (δ ppm, CDCl$_3$); 0.8–1.0(21H, m), 3.7–4.1 (2H, m), 3.8(3H, s), 5.0 (1H, s), 5.15(1H, s), 5.3 (1H, s), 5.5(2H, m) |
| 2 | | Yield: 85% 0.8–1.0(21H, m), 3.6–4.1 (2H, m), 3.8(3H, s), 5.0 (1H, s), 5.15(1H, s), 5.3 (1H, s), 5.5(2H, m) |
| 3 | | Yield: 87% 0.9–1.0(21H, m), 3.5–4.1 (2H, m), 3.75(3H, s), 5.0 (1H, s), 5.2(1H, s), 5.3 (1H, s), 5.5(2H, m) |

-continued

| Run No. | $+CH_2)_n\genfrac{}{}{0pt}{}{R^4}{OR^{31}}R^5$ | Yield NMR (δ ppm, CDCl₃) |
|---|---|---|
| 4 | cyclohexyl-CH(OZ)- (structure with H) | Yield: 75% 0.9–1.0(21H, m), 3.7–4.1 (2H, m), 3.75(3H, s), 5.0 (1H, s), 5.15(1H, s), 5.3 (1H, s), 5.5(2H, m) |
| 5 | t-Bu-C(CH₃)₂-chain-CH(OZ)- | Yield: 91% 0.9–1.0(21H, m), 1.13(6H, s), 3.6–4.1(2H, m), 3.75(3H, s), 5.0(1H, s), 5.15(1H, s), 5.3(1H, s), 5.5(2H, m) |
| 6 | branched alkyl-CH(OZ')- | Yield: 87% 0.9–1.0(12H, m), 1.1(3H, s), 3.7–4.1(2H, m), 3.8(3H, s), 5.0(1H, s), 5.2(1H, s), 5.3(1H, s), 5.5(2H, m) |
| 7 | vinyl-C(Et)(OZ')-pentyl | Yield: 81% 0.9–1.0(12H, m), 3.7–4.1 (2H, m), 3.8(3H, s), 4.7–5.6 (7H, m) |

EXAMPLE 35

In accordance with Example 11, compounds having different

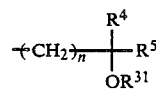

moieties in formula [I] were synthesized as shown in the following table.

| Run No. | $+CH_2)_n\genfrac{}{}{0pt}{}{R^4}{OR^{31}}R^5$ | Yield | Spectrum |
|---|---|---|---|
| 1 | CH₃-CH(OZ)-CH(CH₃)-butyl | 75 | as in Example 3 |
| 2 | CH₃-CH(OZ)-CH₂-CH(CH₃)-propyl | 65 | as in Example 10 |
| 3 | cyclopentyl-CH(OZ)-CH₃ | 60 | as in Example 5 |
| 4 | cyclohexyl-CH(OZ)-CH₃ (with H) | 69 | as in Example 9 |
| 5 | t-Bu-C(CH₃)₂-CH(OZ)-pentyl | 80 | as in Example 8 |
| 6 | branched | 82 | as in Example 4 |
| 7 | vinyl-C(Et)(OZ')-butyl | 55 | as in Example 7 |

EXAMPLE 36

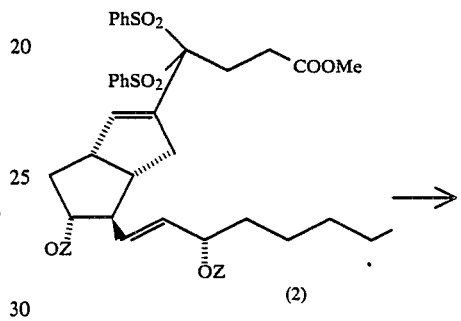

(2)

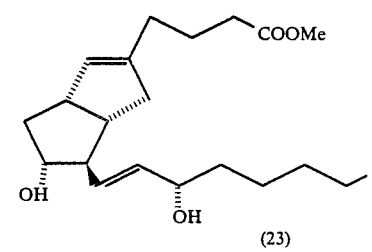

(23)

Anhydrous disodium phosphate (41 mg; 0.29 mmole) was added in a stream of nitrogen to a solution of 62 mg (0.071 mmole) of 4,4-bis(phenylsulfonyl)isocarbacyclin methyl ester-11,15(t-butyldimethylsilyl)ether (2) in 1.5 ml of anhydrous methanol. The mixture was cooled to −30° C. To the solution was added 600 mg of sodium amalgam (6% in Hg), and the mixture was stirred for 2 hours. Furthermore, 200 mg of sodium amalgam was added and the mixture was stirred for 3 hours. The reaction was terminated by adding aqueous ammonium chloride solution, and the reaction mixture was extracted with diethyl ether. The organic layer was washed with saturated aqueous sodium chloride solution, dried over anhydrous magnesium sulfate, and concentrated under reduced pressure. The crude product was subjected to silica gel column chromatography (n-hexane/ethyl acetate=50:1→10:1) to give 36 mg (86%) of isocarbacyclin methyl ester-11,15-bis(t-butyldimethylsilyl)ether. This product agreed in TLC and spectral data with a separately prepared authentic sample.

NMR (δppm, CDCl₃): 0.9 (s+m, 21H), 1.2–2.5 (m, 22H), 3.0 (m, 1H), 3.7 (s, 3H), 3.7–4.1 (m, 2H), 5.3 (m, 1H), 5.55 (m, 2H).

TLC:Rf=0.75 (n=hexane:ethyl acetate=4:1).

To a solution of 35 mg (0.06 mmole) of the resulting isocarbacyclin methyl ester-11,15-bis(t-butyldimethylsilyl)ether in 3 ml of dry THF was added 400 microliters (0.4 mmole) of tetrabutyl ammonium fluoride (1M in THF) at 0° C. Thirty minutes later, the temperature of the mixture was raised to room temperature, and it was stirred at room temperature for 14 hours. Water was added to terminate the reaction. The reaction mixture was extracted with ethyl acetate. The organic layer was washed with saturated aqueous sodium chloride solution, dried over anhydrous magnesium sulfate, and concentrated under reduced pressure to remove the solvent. The crude product was subjected to silica gel column chromatography (n-hexane/ethyl acetate=1:1→1:2) to give 18 mg (85%) of isocarbacyclin methyl ester (23). This produce agreed in HPLC, TLC and spectral data with a separately synthesized authentic sample.

NMR (δppm, CDCl$_3$): 0.9 (m, 3H), 1.2–2.5 (m, 24H), 3.0 (m, 1H), 3.7 (s, 3H), 3.7–4.1 (m, 2H), 5.3 (m, 1H), 5.55 (m, 2H).

TLC:Rf=0.5 (n=hexane:ethyl acetate=1:4).

HPLC: (Zorbax-SIL 2.5% ethanol hexane 1.3 ml/min.)

EXAMPLE 37

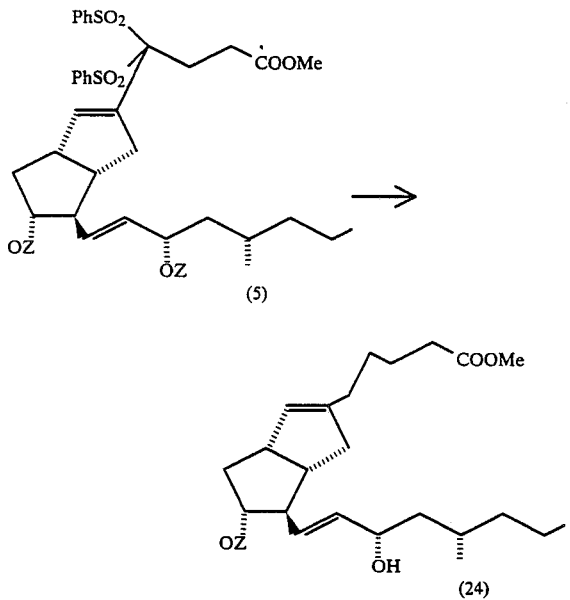

Anhydrous disodium phosphate (228 mg; 0.2 mmole) was added to a solution of 45 mg (0.05 mmole) of 17(S), 20-dimethyl-4,4-bis(phenylsulfonyl)isocarbacyclin methyl ester-11,15-bis(t-butyldimethylsilyl)ether (5) in 1.5 ml of anhydrous methanol, and the mixture was cooled to −30° C. Sodium agalgam (6% in Hg; 600 mg) was added, and the mixture was stirred for 6 hours.

The reaction was terminated by adding aqueous ammonium chloride solution, and the reaction mixture was extracted with diethyl ether. The organic layer was washed with saturated aqueous sodium chloride solution, and dried over anhydrous magnesium sulfate. The solvent was evaporated under reduced pressure. The crude product was subjected to silica gel column chromatography (n-hexane:ethyl acetate=50:1→10:1) to give 24 mg (79%) of 17(S), 20-dimethylisocarbacyclin methyl ester-11,15-bis(t-butyldimethylsilyl)ether (24). This product agreed in LC and spectral data with a separately synthesized authentic sample.

NMR (δppm, CDCl$_3$): 0.9 (s+m, 21H), 1.0–2.5 (m, 26H), 3.0 (m, 1H), 3.7 (s, 3H), 3.7–4.1 (m, 2H), 5.3 (m, 1H), 5.55 (m, 2H).

TLC:Rf=0.75 (n=hexane:ethyl acetate=4:1).

EXAMPLE 38

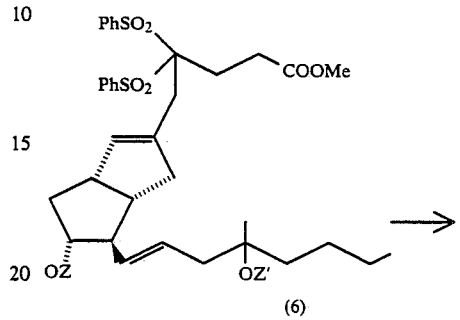

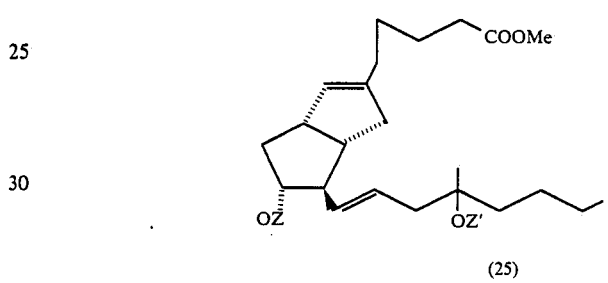

Anhydrous disodium phosphate (24 mg; 0.17 mmole) was added in a stream of nitrogen to a solution of 34 mg (0.04 mmole) of 15-deoxy-16-methyl-16-hydroxy-4,4-bis(phenylsulfonyl)isocarbacyclin methyl ester-11-t-butyldimethylsilyl ether-16-trimethylsilyl ether (6) in 1 ml of anhydrous methanol, and the mixture was cooled to −30° C. Four hundred milligrams of sodium amalgam (6% in Hg) was added, and the mixture was stirred for 7 hours. The reaction was terminated by adding aqueous ammonium chloride solution, and the reaction mixture was extracted with diethyl ether. The organic layer was washed with saturated aqueous sodium chloride solution and dried over anhydrous magnesium sulfate. The solvent was evaporated under reduced pressure. The crude product was subjected to silica gel column chromatography (n-hexane/ethyl acetate=50:1→10:1) to give 17 mg (75%) of 15-deoxy-16-methyl-16-hydroxyisocarbacyclin methyl ester-11-t-butyldimethylsilyl ether-16-trimethylsilyl ether. This product agreed in TLC and spectra data with an authentic sample separated synthesized.

NMR (δppm, CDCl$_3$): 0.9 (s+m, 12H), 1.1 (s, 3H), 1.2–2.5 (m, 22H), 3.0 (m, 1H), 3.65 (s, 3H), 3.8–4.0 (m, 1H), 5.3 (m, 1H), 5.55 (m, 2H).

TLC:Rf=0.75 (n=hexane:ethyl acetate=4:1).

EXAMPLE 39

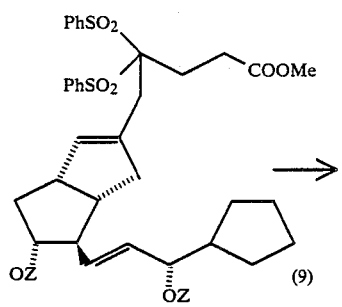
(9)

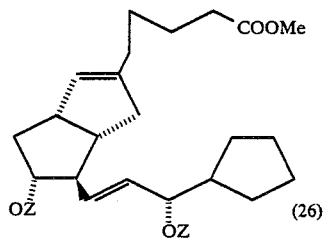
(26)

Anhydrous disotium phosphate (36 mg; 0.25 mmole) was added in a stream of nitrogen to a solution of 51 mg (0.059 mmole) of 16,17,18,19,20-pentanor-15-cyclopentyl-4,4-bis(phenylsulfonyl)isocarbacyclin methyl ester-11,15-bis(t-butyldimethylsilyl)ether (9), and the mixture was cooled to −30° C. Six hundred milligrams of sodium amalgam (6% in Hg) was added, and the mixture was stirred for 5 hours. The reaction was terminated by adding aqueous ammonium chloride solution. The reaction mixture was extracted with diethyl ether, and the organic layer was washed with saturated aqueous sodium chloride solution, and dried over anhydrous magnesium sulfate. The solvent was evaporated under reduced pressure. The crude product was subjected to silica gel column chromatography (n-hexane/ethyl acetate=50:1→10:1) to give 25 mg (75%) of 16,17,18,19,20-pentanor-15-cyclopentylisocarbacyclin methyl ester-11,15-bis(t-butyldimethylsilyl)ether. This product agreed in TLC and spectral data with a separately synthesized authentic sample.

NMR (δppm, CDCl$_3$): 0.9 (s, 18H), 1.0-2.5 (m, 23H), 3.0 (m, 1H), 3.7 (s, 3H), 3.7-4.1 (m, 2H), 5.3 (m, 1H), 5.55 (m, 2H).

TLC:Rf=0.75 (n=hexane:ethyl acetate=4:1).

EXAMPLE 40

The disilyl compounds obtained in Examples 37 to 39 were deprotected as in Example 36.

The NMR spectra of the deprotected products are shown below.

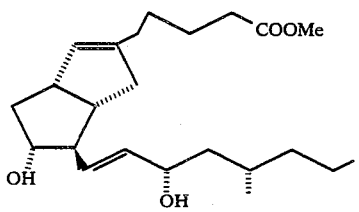
(i)

(δppm, CDCl$_3$): 0.9 (m, 3H), 1.0-2.5 (m, 28H), 0.3 (m, 1H), 3.7 (s, 3H), 3.0-4.1 (m, 2H), 5.3 (m, 1H), 5.55 (m, 2H).

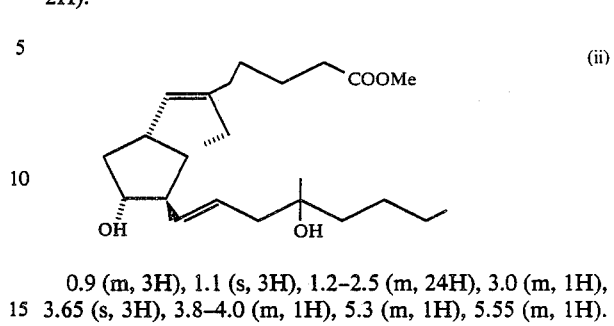
(ii)

0.9 (m, 3H), 1.1 (s, 3H), 1.2-2.5 (m, 24H), 3.0 (m, 1H), 3.65 (s, 3H), 3.8-4.0 (m, 1H), 5.3 (m, 1H), 5.55 (m, 1H).

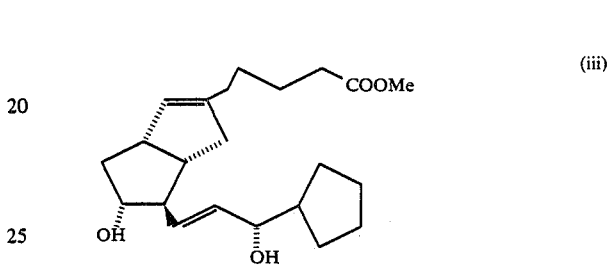
(iii)

1.0-2.5 (m, 25H), 3.0 (m, 1H), 3.7 (s, 3H), 3.7-4.1 (m, 2H), 5.3 (m, 1H), 5.55 (m, 1H).

EXAMPLE 41

Dry methanol (90 ml) was added to 3.31 g (0.14 gram-atom) of magnesium metal, and the mixture was stirred at room temperature in an atmosphere of nitrogen. Then, a solution of 11.9 g (13.6 mmole) of the bissulfonyl compound (2) in 180 ml of dry methanol was added. The mixture was stirred while being warmed over an oil bath. When the solvent began to reflux, the oil bath was removed, and the mixture was stirred for 30 minutes while spontaneously refluxing the solvent at room temperature. Saturated aqueous ammonium chloride solution (450 ml) was added, and the reaction mixture was extracted twice with 600 ml of ethyl acetate. The organic layers were combined, washed with 300 ml of saturated aqueous potassium hydrogensulfate solution, 300 ml of saturated aqueous sodium bicarbonate solution and 300 ml of saturated aqueous sodium chloride solution, and dried over anhydrous magnesium sulfate. The solvent was evaporated, and the resulting crude product (8.23 g) was purified by silica gel column chromatography to give 6.52 g (yield 81%) of the desulfonylated compound (27) in eluates obtained with 7:1 hexane-ethyl acetate).

NMR ($\delta_{TMS}^{CDCl_3}$): 0.8–1.0 (21H), 2.88 (1H, m), 3.67 (3H, s), 3.74 (1H, m), 4.06 (1H, br), 5.25 (1H, brs), 5.48 (2H, m).

EXAMPLE 42-a (2R,3R,4R)-4-t-butyldimethylsilyloxy-3-[(E,3S)-3-t-butyldimethylsilyloxy-1-octenyl]-2-(3-trimethylsilyl-2-propynyl)cyclopentanone:

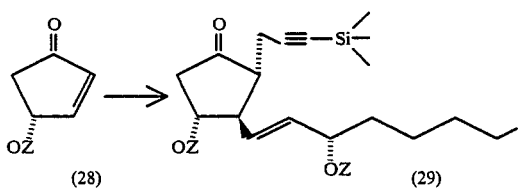

t-Butyllithium (1.7M, 194 ml, 330 mmoles) was put in a 2-liter three-necked flask purged with argon, and cooled to −78° C. Separately, 60.58 g (165 mmoles) of (E,3S)-3-t-butyl dimethylsilyloxy-1-iodo-1-octene was taken into a 200 ml of an eggplant-shaped flask, cooled to −78° C., and dried under reduced pressure. The eggplant-shaped flask was purged with nitrogen, and 100 ml of dry diethyl ether was put into it, and cooled to −78° C. The ether solution was then added to the t-butyllithium in the three-necked flask mentioned above by means of a stainless steel tube under argon pressure. The mixture was stirred at −78° C. for 3 hours. Separately, a 500 ml eggplant-shaped flask was charged with 31.43 g (165 mmoles) of cuprous iodide. The inside of the flask was dried under reduced pressure and again purged with argon. 220 ml of THF and 90.3 ml (363 mmoles) of tributylphosphine were added, and stirred at 25° C. to form a uniform solution. The uniform solution was cooled to −78° C. The uniform solution was cooled to −78° C., and then added by means of a stainless steel tube under argon pressure to the previously prepared alkenyllithium solution. This solution was also stirred at −78° C. for 1 hour. Then, a solution of 31.86 g (150 mmoles) of (R)-4-t-butyldimehylsilyloxy-2-cyclopentenone (28) in 220 ml of THF was added at −78° C. over the course of 2 hours by means of a stainless steel tube. The reaction solution was heated to −50° C., stirred for 30 minutes, and again cooled to −78° C. Then, 144 ml of hexamethylphosphoric triamide was added, and the mixture was further stirred at −78° C. for 30 minutes. A solution of 69.39 g (180 mmoles) of triphenyltin chloride in 160 ml of THF was added at a time at −78° by using a stainless steel tube. The mixture was then heated to −30° C., and 55.53 g (233 mmoles) of 3-iodo-1-trimethylsilyl-1-propyne was added, and the mixture was stirred for 1.5 hours. The reaction mixture was poured into 700 ml of saturated aqueous ammonium chloride solution. Furthermore, 500 ml of n-hexane was added, and the mixture was vigorously stirred. The organic layer was washed with saturated aqueous sodium chloride solution and dried over anhydrous magnesium sulfate, followed by filtration and concentration under reduced pressure. To the resulting solution was added 700 ml of n-hexane, and 5 ml portions of 35% hydrogen peroxide solution (total 60 ml) were added to oxidize tributylphosphine. The insoluble materials were removed by filtration through Celite. The filtrate was transferred to a separating funnel. The organic layer was washed with an equal amount mixture of aqueous ammonia and a saturated aqueous solution of ammonium chloride to remove the copper ion. The organic layer was then washed with saturated aqueous ammonium chloride solution and saturated aqueous sodium chloride solution, dried over anhydrous magnesium sulfate, filtered, and concentrated under reduced pressure to give 127 g of a crude product. The crude product was subjected to silica gel column chromatography (Daiso Gel IR-60, 1800 g; hexane/benzene−1:1) to give 55.0 g (yield 65%) of (2R,3R,4R)-4-t-butyldimethylsilyloxy-3-[(E,3S)-3-t-butyldimetylsilyloxy-10-octenyl]-2-(3-trimethylsilyl-2-propynyl)cyclopentanone (29).

TLC:Rf=0.57 (benzene).

IR (liquid film): cm$^{-1}$. 2980, 2960, 2880, 2200, 1755, 1720, 1470, 1460.

EI-MS: m/e 564 (M+), 507 (M-$^t$Bu)+.

$^1$H-NMR (CCl$_4$): δ(ppm) 0.07 (s, 12H, Si(CH$_3$)$_2$×2), 0.13 (s, 9H, Si(CH$_3$)$_3$), 0.89 (s, 18H, SiC(CH$_3$)$_3$×2), 0.8–1.6 (m, 11H, —(CH$_2$)$_4$CH$_3$), 1.6–3.0 (m, 6H), 3.7–4.2 (m, 2H, CHOSi×2), 5.3–5.6 (m, 2H, —CH═CH—).

EXAMPLE 42-b (1R,2R,3R)-1-t-butyldimethylsilyloxy-2-[(E,3S)-3-t-butyldimethylsilyloxy-1-octenyl]-4-methylene-3-(3-trimethylsilyl-2-propynyl)cyclopentane:

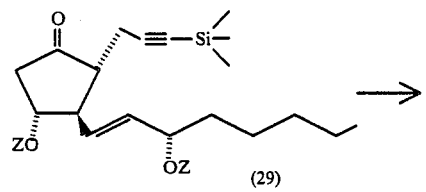

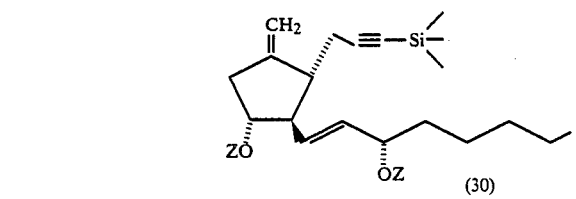

70.0 g (124 mmoles) of (2R,3R,4R)-4-t-butyldimethylsilyloxy-3-[(E,2S)-3-t-butyldimethylsilyloxy-1-octenyl]-2-(3-trimethylsilyl-2-propynyl)cyclopentnone (29) was dissolved in 400 ml of methylene chloride, and a suitable amount of a methylenation agent prepared from zinc, dibromomethane and titanium tetrachloride in accordance with the method of Lombardo (see Tetrahedron Letters, vol. 23, page 4293, 1982) was added. The mixture was stirred at room temperature for 10 minutes, and the disappearance of the starting material was checked by thin layer chromatography (TLC). The methylenation agent was added several times until the starting material disappeared. After the reaction, the liquid layer of the reaction mixture was taken out by decantation. The remaining solid was washed twice with methylene chloride, and the washings were taken out by decantation. To the liquid layer was added n-hexane in a nearly equal amount, and the mixture was transferred to a separating funnel. It was washed successively with 10% aqueous tartaric acid solution, saturated aqueous sodium hydrogen carbonate solution and saturated sodium chloride solution. The organic layer was dried over anhydrous magnesium sulfate, and the solvent was evaporated. There was obtained 66.5 g of a crude product. When the crude product was purified by silica gel column chromatography, 58.9 g (yield 84%) of (1R,2R,3R)-1-t-butyldimethylsilyloxy-2-[(E,3S)-3-t-butyldimethylsilyloxy-1-octenyl]-4-methylene-3-(3-trimethylsilyl-2-propynyl)cyclopentane (30) from eluates obtained with 1.5% ethyl acetate/n-hexane.

TLC:Rf=0.74 (ethyl acetate/n-hexane=1:19).

IR (liquid film): cm$^{-1}$ 3090, 2200, 1658, 1460, 1250.

EI-MS: m/e 562 (M+), 505 (M-$^t$Bu)+.

$^1$H-NMR (CDCl$_3$): δ(ppm) 0.06 (s, 12H, Si(CH$_3$)$_2$×2), 0.13 (s, 9H), Si(CH$_3$)$_3$), 0.89 (s, 18H, SiC(CH$_3$)$_3$×2), 0.8–1.6 (m, 11H, —CH$_2$CH$_2$CH$_2$CH$_3$), 2.1–3.0 (m, 6H), 3.8–4.25 (m, 2H, CHOSi×2), 5.05 (d, 2H, J=9 Hz, =CH$_2$), 5.45–5.6 (m, 2H, CH=CH).

EXAMPLE 42-c (1R,2R,3R,4S)-1-t-butyldimethylsilyloxy-2-[(E,3S)-3-t-butyldimethylsilyloxy-1-octenyl]-4-hydroxymethyl-3-(3-trimethylsilyl-2-propynyl)cyclopentane:

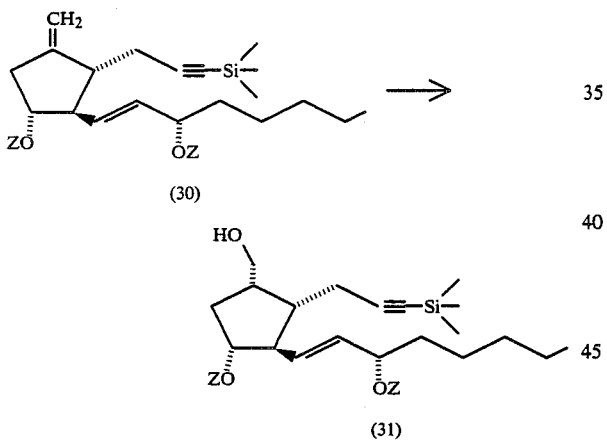

The inside of a 2-liter eggplant-shaped flask was purged with nitrogen gas, and 11.20 g (91.8 mmoles) of 9-BBN(9-borabicyclo[3.3.1]nonane) dimer was taken into the flask. Freshly distilled THF (170 ml) was added to form a solution. The reaction solution was cooled with ice, and a solution of 39.70 g (70.6 mmoles) of (1R,2R,3R)-1-t-butyldimethylsilyloxy-2-[(E,3S)-3-t-butyldimethylsilyloxy-1-octenyl]-4-methylene-3-(3-trimethylsilyl-2-propynyl)cyclopentane (30) in 50 ml of THF was added. The mixture was stirred at room temperature for 1 hour. The reaction solution was again cooled with ice, and 56 ml of a 5N aqueous solution of sodium hydroxide and then 56 ml of 35% hydrogen peroxide solution were added. The reaction mixture was stirred at 50° C. for 30 minutes, poured into ice water, and extracted twice with ethyl acetate. The organic layers were washed successively with saturated aqueous sodium hydrogen carbonate solution and saturated aqueous sodium chloride solution, and dried over anhydrous magnesium sulfate. The solvent was evaporated under reduced pressure. The residue was purified by silica gel coluimn chromatography to obtain 33.5 g (yield 82%) of (1R,2R,3R,4S)-1-t-butyldimethylsilyloxy-2-[(E,3S)-3-t-butyldimethylsilyloxy-1-octenyl]-4-hydroxymethyl-3-(3-trimethyl silyl-2-propynyl)cyclopentane (31) from eluates obtained with 5% ethyl acetate/n-hexane.

TLC:Rf=0.53 (ethyl acetate/n-hexane=1:6).

IR (liquid film): cm$^{-1}$ 3150-3600, 2200, 1460, 1250.

EI-MS: m/e 581 (M+H)+, 580 (M)+, 523 (M-$^t$Bu)+.

$^1$H-NMR δ(CDCl$_3$): (ppm) 0.04 (s, 12H, Si(CH$_3$)$_2$×2), 0.13 (s, 9H), Si(CH$_3$)$_3$), 0.89(s, 18H, SiC(CH$_3$)$_3$×2), 0.77–1.65 (m, 11H, —(CH$_2$)$_4$CH$_3$), 2.75–3.05 (br, 1H, —OH), 3.7–3.9 (m, 2H, —CH$_2$O—), 3.9–4.12 (m, 2H, CHOSi×2), 5.33–5.53 (m, 2H, —CH=CH—).

EXAMPLE 42-d (1R,2R,3R,4S)-1-t-butyldimethylsilyloxy-2-[(E,3S)-t-butyldimethylsilyloxy-1-octenyl]-4-hydroxymethyl-3-(2-propynyl)cyclopentane:

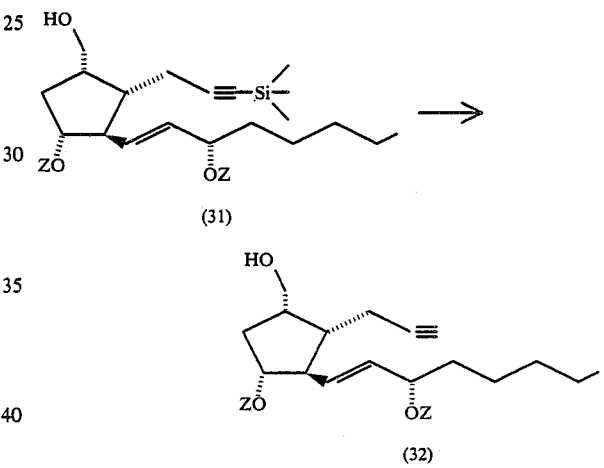

6.40 g (110 mmoles) of (1R,2R,3R,4S)-1-t-butyldimethylsilyloxy-2-[(E,3S)-3-t-butyldimethylsilyloxy-1-octenyl]-4-hydroxymethyl-3-(3-trimethylsilyl-2-propynyl)cyclopentane (31) was taken into a 1-liter eggplant-shaped flask, and dissolved by adding 500 ml of methanol. Then, 106.3 g of a 28% methanol solution of sodium methylate was added, and the mixture was stirred at room temperature for 30 minutes. Saturated aqueous ammonium chloride solution (300 ml) was added, and the mixture was extracted twice with ethyl acetate. The organic layer was successively washed with saturated aqueous potassium hydrogensulfate solution, saturated aqueous sodium bicarbonate solution and saturated aqueous sodium chloride solution and dried over anhydrous magnesium sulfate. The solvent was evaporated under reduced pressure. The residue was purified by silica gel column chromatography to obtain 53.9 g (yield 96%) of (1R,2R,3R,4S)-1-t-butyldimethylsilyloxy-2-[(E,3S)-3-t-butyldimethylsilyloxy-1-octenyl]-4-hydroxymethyl-3-(2-propynyl)cyclopentane (32) from eluates obtained with 10% ethyl acetate/n-hexane.

TLC:Rf=0.40 (ethyl acetate/n-hexane=1:6).

IR (liquid film): cm$^{-1}$ 3600–3100, 3320, 2980, 2950, 2870, 2120, 1460, 1430, 1255.

EI-MS: m/e 508 (M)+, 451 (M-$^t$Bu)+.

$^1$H-NMRδ(CDCl$_3$): (ppm) 0.03 (s, 12H, Si(CH$_3$)$_2$×2), 0.87 (s, 18H, SiC(CH$_3$)$_3$×2), 0.8–1.8 (m, 11H, —(CH$_2$)$_4$CH$_3$), 1.94 (t, 1H, J=3 Hz, —C≡C—H), 2.31 (d, 2H, J=3 Hz, —CH$_2$'C≡C), 2.0–2.47 (m, 5H), 2.85–3.13 (br, 1H, —OH), 3.6–3.9 (m, 2H, —CH$_2$O—), 3.9–4.2 (m, 2H, CHOSi×2), 5.37–5.52 (m, 2H, —CH=CH—).

EXAMPLE 42-e (1R,2R,3R,4S)-1-t-butyldimethylsilyloxy-2-[(E,3S)-3-t-butyldimethylsilyloxy-1-octenyl]-4-formyl-3-(2-propynyl)cyclopentane:

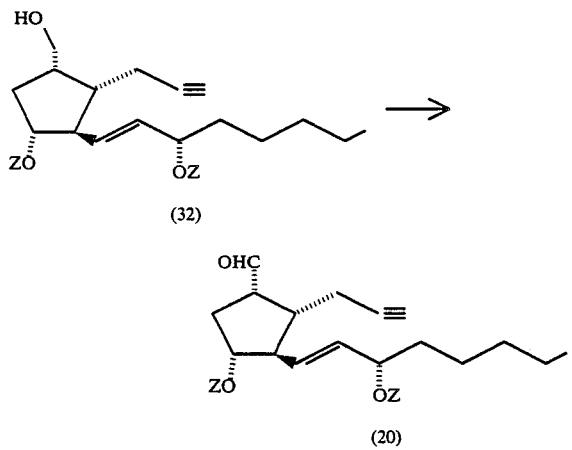

Oxalyl chloride (5.08 g; 40 mmoles) and 60 ml of dichloromethane were taken into a nitrogen-purged 500 ml eggplant-shaped flask, and cooled to −50° C. A solution of 6.24 g (80 mmoles) of dimethyl sulfoxide in 20 ml of dichloromethane was added, and the mixture was stirred for 30 minutes. A solution of 9.09 g (17.9 mmoles) of (1R,2R,3R,4S)-1-t-butyldimethylsilyloxy-2-[(E,3S)-3-t-butyldimethylsilyloxy-1-octenyl]-4-hydroxymethyl-3-(2-propynyl)cyclopentane (32) in 40 ml of dichloromethane was added, and the mixture was stirred at −50° C. for 30 minutes. Subsequently, 10.1 g (100 mmoles) of triethylamine was added, and the mixture was stirred at −50° C. for 30 minutes. Acetic acid (7.2 g; 120 mmoles) was added, and the mixture was stirred for 10 minutes. The reaction mixture was poured into saturated aqueous ammonium chloride solution and extracted with dichloromethane. The organic layer was washed successively with saturated aqueous potassium hydrogensulfate and saturated aqueous sodium chloride solution, and dried over anhydrous magnesium sulfate. The solvent was evaporated under reduced pressure to give 9.05 g (yield of the crude product 100%) of (1R,2R,3R,4S)-1-t-butyldimethylsilyloxy-2-[(E,3S)-3-t-butyldimethylsilyloxy-1-octenyl]-4-formyl-3-(2-propynyl)cyclopentane (20).

TLC:Rf=0.65 (n-hexane:ethyl acetate=4:1).

$^1$H-NMRδ(CDCl$_3$): (ppm) 0.07 (s, 12H, Si(CH$_3$)$_2$×2), 0.87 (s, 18H, SiC(CH$_3$)$_3$×2), 0.7–1.8 (m, 11H, —(CH$_2$)$_4$CH$_3$), 1.8–2.4 (m, 7H), 2.65–3.1 (m, 1H, —CHCO—), 3.6–4.2 (m, 2H, —CHOSi×2), 5.2–5.45 (m, 2H, —CH=CH—), 9.75 (d, 1H, J=3 Hz, —CHO).

EXAMPLE 43-a

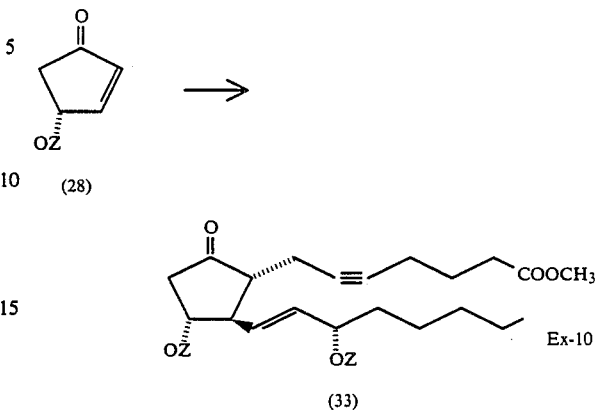

An argon-purged 150 ml reaction tube was charged with 593.1 mg (1.61×10$^{-3}$ mole) of (E)-1-iodo-3-t-butylsilyloxy-1-octene and 6 ml of dry diethyl ether, and the mixture was stirred at −95° C. Then, 1.72 ml (3.22×10$^{-3}$ mole) of t-butyllithium (1.87M pentane) was added via syringe, and the mixture was stirred at −95° to −78° C. for 3 hours. Separately, 306.6 mg (1.61×10$^{-3}$ mole) of cuprous iodide was taken into a 30 ml eggplant-shaped flask, and the inside of the flask was dried by heating under reduced pressure and then purged with argon. Dry THF (6 ml) and 1.04 ml (4.19×10$^{-3}$ mole) of tributylphosphine were introduced into the flask and the entire mixture was stirred at 23° C. to form a uniform solution. The solution was cooled to −78° C. and added at a time under argon pressure to the vinyllithium solution prepared previously. Furtehrmore, 6 ml of dry THF was added by washing the flask with it. The mixture was stirred at −78° C. for 10 minutes, a solution of 325.6 mg (153×10$^{-3}$ mole) of 4-t-butyldimethylsiloxy-2-cyclopentenone in 12 ml of THF was added dropwise over 1 hour. The flask was washed with 1 ml of THF, and the mixture was stirred for 10 minutes. HMPA (1.5 ml) was added, and the mixture was stirred for 30 minutes. Then, a THF solution (2 ml) of 627.6 mg (1.61×10$^{-3}$ mole) of triphenyltin chloride was added. The mixture was heated to −30° C., and an HMPA solution of 814.2 mg (3.06×10$^{-3}$ mole) of 1-iodo-6-carbomethoxy-2-hexyne was added, and the mixture was stirred at −30° C. for 4.5 hours. The reaction mixture was subsequently left to stand at −27° C. for 13 hours, and 20 ml of saturated aqueous ammonium chloride solution was added. The mixture was vigorously shaken and separated into an organic layer and an aqueous layer. The aqueous layer was extracted twice with 20 ml of diethyl ether. The ether layers were combined, washed with saturated aqueous sodium chloride solution, and dried over anhydrous sodium sulfate. The dried solution was filtered, concentrated under reduced pressure and subjected to silica gel column chromatography (Merck 7734, 50 g; 1:60=ethyl acetate:hexane, 600 ml→1:20=ethyl acetate:hexane, 200 ml) to give 542.1 mg (yield 59.7%) of 11,15-bis(t-butyldimethylsilyl)-5,6-dehydroprostaglandin E$_2$ methyl ester (33).

TLC:Rf=0.50 (ethyl acetate/hexane=1:5).

IR (liquid film): 1746, 1246, 827, 767 cm$^{-1}$.

$^1$H NMR (CDCl$_3$–CCl$_4$=1:1)δ: 0.04 and 0.06 (each s, 12, SiCH$_3$×2), 0.89 (s, 18, SiC(CH$_3$)$_3$×2), 0.92 (t, 1, J=6.5 Hz, CH$_3$), 1.1–1.5 (m, 8, CH$_2$×4), 1.7–2.9 (m, 12, CH$_2$CO×2, CH$_2$C≡×2, CH×2 and CH$_2$), 3.65 (s, 3, OCH$_3$), 4.05 (m, 2, CHOSi×2), 5.4–5.7 (m, 2, vinyl).

$^{13}$C NMR (CDCl$_3$)δ: −4.7, −4.5, −4.2, 13.6, 14.0, 16.9, 18.0, 18.2, 22.6, 24.2, 25.0, 25.8, 25.9, 31.9, 32.7, 38.6, 47.7, 51.4, 51.9, 52.9, 72.7, 73.1, 77.3, 80.8, 128.2, 136.8, 173.4, 213.4.

[α]$_D^{21}$; −13.9° (C 1.59, CH$_3$OH).

EXAMPLE 43-b

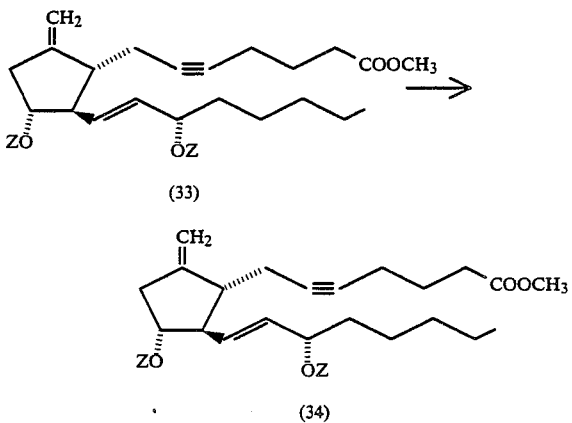

An aliquot (1.33 g; 2.25 mmoles) of 11,15-bis(t-butyldimethylsilyl)-5,6-dehydroprostaglandin E$_2$ methyl ester (33) obtained in Example 43-a was dissolved in 30 ml of methylene chloride. Under ice cooling, a suitable amount of a methylenation agent prepared in accordance with the method of Lombardo et al. from zinc, dibromomethane and titanium tetrachloride (see Tetrahedron Letters, vol. 23, page 4293, 1982) was added. With stirring at room temperature, the disappearance of the starting material was checked by thin layer chromatography (TLC) and the end point of the reaction was determined. (The total reaction time was 45 minutes.) The reaction mixture was added to 150 ml of saturated aqueous sodium bicarbonate solution, filtered through Celite, and extracted twice with n-hexane. The organic layers were combined, washed with saturated aqueous sodium chloride solution, and dried over anhydrous magnesium sulfate. The solvent was evaporated to give 1.2 g of a residue. The residue was purified by silica gel chromatography to obtain 928 mg (yield 70%) of 11,15-bis(t-butyldimethylsilyl)-5,6-dehydro-9-deoxy-9-methyleneprostaglandin E$_2$ methyl ester (34) from eluates obtained with 2% ethyl acetate/n-hexane.

NMR (δppm, CDCl$_3$): 0.75–1.0 (21H), 3.67 (3H, s), 3.6–4.3 (2H, m), 4.8–5.2 (2H, br), 5.3–5.7 (2H, m).

IR (cm$^{-1}$, neat): 2960, 2940, 2860, 1740, 1458, 1428, 1250, 1112, 1000, 965, 835, 773.

EXAMPLE 43-c

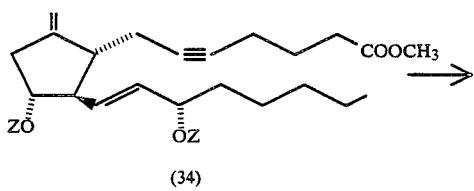

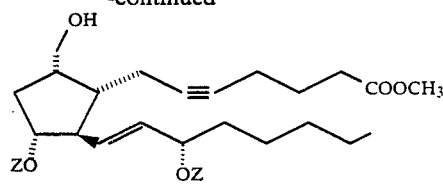

The compound (34) (416 mg) was dissolved in 15 ml of dry THF, and the solution was cooled to 0° C. A 0.5M hexane solution of 9-BBN(9-borabicyclo[3.3.1]nonane) (5.64 mg) was added dropwise, and the mixture was stirred at 0° C. for 2.5 hours. 3N—NaOH (1.2 ml) and then 1.0 ml of 30% H$_2$O$_2$ were added. The mixture was stirred at 0° C. for 10 minutes and at 25° C. for 30 minutes. A saturated aqueous solution of sodium sulfate was added to the reaction mixture, and the mixture was extracted three times with 20 ml of diethyl ether. The organic layers were treated in a customary manner to form a crude product. The crude product was subjected to silica gel column chromatography (40 g of silica gel; hexane:ethyl acetate=7:1) to give 327 mg (yield 76%) of the product (35).

TLC:Rf=0.46 (hexane/ethyl acetate=2:1).

IR (CHCl$_3$ solution, cm$^{-1}$): 3400, 2840, 1760, 1360, 820.

$^1$H NMR (CDCl$_3$ 90 MHZ, ppm)δ: 0.40–0.10 (s, 12, Si CH$_3$×4), 0.70–1.40 (s, 21, SiC(CH$_3$)$_3$×2&CH$_3$), 1.10–2.58 (m, 19, CH$_2$×9, OH), 3.70 (s, 3, OCH$_3$).

EXAMPLE 43-d

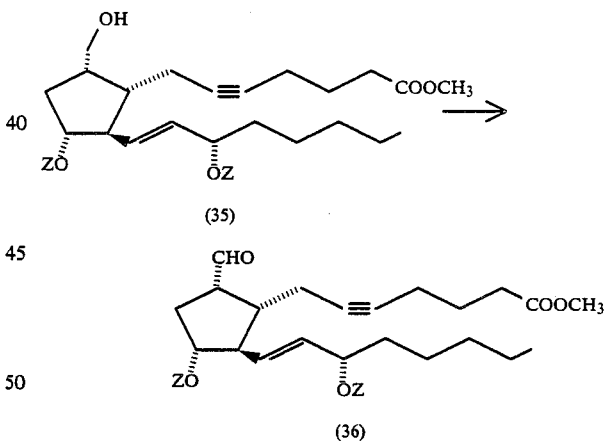

Seven mg of PDC (pyridinium dichromate) was added at room temperature to 46 mg of the compound (35) dissolved in 10 ml of dichloromethane, and the mixture was stirred for 11 hours. The insoluble materials were removed from the reaction mixture by filtration, and the filtrate was concentrated to give a crude product. The crude product was purified by column chromatography (silica gel 5 g; hexane:ethyl acetate=10:1) to give 38 mg (yield 85%) of the product (36).

TLC:Rf=0.59 (n-hexane/ethyl acetate=2/1).

$^1$H NMR (CDCl$_3$ 90 MHZ, ppm)δ: 0.02–0.10 (s, 12, SiCH$_3$×4), 0.66–1.01 (s, 21, SiC(CH$_3$)$_3$×2&CH$_3$), 1.01–2.64 (m, 21, CH$_2$×9, &CH×3), 3.64 (s, 3, OCH$_3$), 3.74–4.18 (m, 2, SiOCH×2), 5.28–5.50 (m, 2, vinyl), 9.95 (d, J=2.93 Hz, 1, CHO).

EXAMPLE 43-e

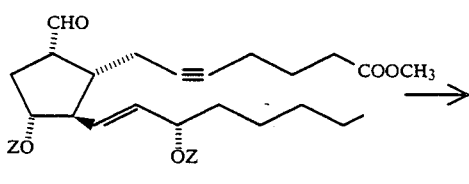

(36)

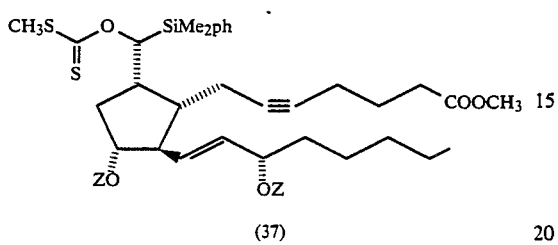

(37)

(A) A 0.28M diethyl ether solution (0.15 ml) of bis(-dimethylphenylsilyl) copper lithium was slowly added at −78° C. to 1.5 ml of a THF solution of 19.4 mg of the aldehyde (36), and the mixture was stirred for 20 minutes. Carbon disulfide (0.004 ml) was added at this temperature, and 5 minutes later, 0.06 ml of HMPA was added. The mixture was further stirred for 30 minutes. Methyl iodide (0.004 ml) was added, and the mixture was stirred for 40 minutes. To the reaction mixture was added 1.5 ml of saturated aqueous ammonium chloride solution, and the mixture was extracted with diethyl ether. The ether extract was worked up in a customary manner to give a crude product. The crude product was purified by column chromatography (silica gel 5 g; hexane:ethyl acetate=20:1) to give 4.8 mg (yield 18%) of the product (37) and further 6.1 mg (yield 28%) of the alcohol compound in which the

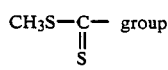 group was changed to a hydrogen atom. This alcohol compound could be converted to the desired product (37) (yield 22%) by treating it with n-butyllithium and then on HMPA, CS$_2$ and CH$_3$.

Spectral data of comound (37) were as follows:

$^1$H NMR (270 MHz, CDCl$_3$)δ: 0.1–0.1 (m, 12, OSiCH$_3$×4), 0.40, 0.44 (s, each, 6, SiCH$_3$×2), 0.7–1.0 (m, 21, OSiC(CH$_3$)$_3$×2, CH$_3$), 1.0–2.6 (m, 21, CH$_2$×9, CH×3), 2.50 (S, 3, SCH$_3$), 3.68 (s, 3, OCH$_3$), 3.6–3.8 (m, 1, C(15)H), 3.9–4.1 (m, 1, C(11)H), 5.20 (dd, 1, J=15.5, 7.7 Hz, C(13)H), 5.37 (dd, 1, J=15.5, 5.6 Hz, C(14)H), 6.38 (d, 1, J=2.3 Hz, CH(Si)O), 7.3–7.6 (m, 5, aromatic).

(B) Thirty mg of the aldehyde (36) was reacted in 2 ml of THF with bis(dimethylphenylsilyl)copper lithium prepared from 18.8 mg of copper cyanide and 0.75 ml of dimethylphenylsilyl lithium (0.56M). Twenty minutes later, the reaction mixture was treated with saturated aqueous ammonium chloride solution and extracted with diethyl ether. The extract was worked up in a customary manner. The crude product was purified by silica gel column chromatography to give 26.8 mg (yield 73.6%) of the alcohol compound.

The spectral data of the alcohol compound were as follows:

$^1$H NMR (270 MHz, CDCl$_3$, δ): 0.015, 0.01, 0.03 (s, each, 12, OSiCH$_3$×2), 0.36, 0.37 (s, each, 6 SiCH$_3$×2), 0.7–1.0 (m, 21, SiC(CH$_3$)$_3$×2, CH$_3$), 1.1–2.5 (m, 22, CH$_2$×9, CH×3, OH), 3.67 (s, 3, OCH$_3$), 3.8–4.1 (m, 3, CHO×2, CH(Si)O), 5.2–5.5 (m, 2, vinyl), 7.3–7.6 (m, 5, aromatic).

The resulting alcohol compound was treated in 2.6 ml of THF with 0.026 ml of n-butyllithium (1.36M hexane solution), 0.08 ml of carbon disulfide, 0.08 ml of methyl iodide and 0.08 ml of HMPA at −78° C. The reaction mixture was worked up in a customary manner to give 16.6 mg (yield 57%) of the desired product (37).

EXAMPLES 43-f

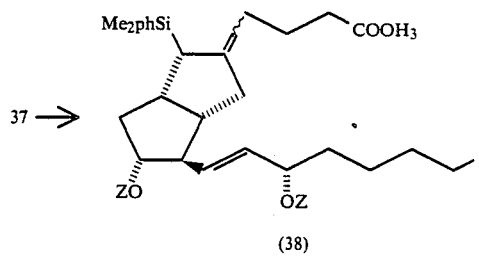

37 →

(38)

(A) Two milligrams of the compound (37) was treated in 0.5 ml of benzene with 20 mg of tri-n-butyltin hydride and 15 mg of (t-BuO)$_2$ at 65° C. for 15 hours and then at 80° C. for 20 hours. The resulting crude product was purified by column chromatography (silica gel 4 g; hexane:ethyl acetate=50:1, 20:1) to give 0.7 mg (yield about 30%) of the desired product (38).

The spectral data of the compound (38) were as follows:

$^1$H NMR (270 MHz, CDCl$_3$)δ: 0.1–0.1 (m, 12, OSiCH$_3$×4), 0.2–0.3 (m, 6, SiCH$_3$×2), 0.8–1.0 (m, 21, SiC(CH$_3$)$_3$×2, CH$_3$), 1.0–2.7 (m, 22, CH$_2$×9, CH×4), 3.65, 3.67 (s, each, 3, OCH$_3$), 3.9–4.1 (m, 2, CH×2), 4.9–5.0, 5.0–5.1 (m, 1, C(5)H), 5.3–5.5 (m, 2, C(13)H, C(14)H), 7.2–7.5 (m, 5, aromatic).

(B) The compound (37) (11 mg) was treated in 10 ml of toluene with 0.16 ml of tri-n-butyltin hydride and 60 mg of (t-BuO)$_2$ at 80° C. for 17 hours, and then purified by column chromatography to give 9 mg (yield 94%) of the desired product (38).

EXAMPLE 43-g

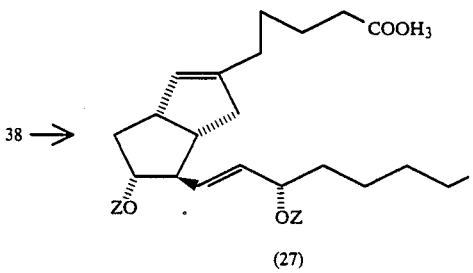

38 →

(27)

Trifluoroacetic acid (10 mg) was added to a solution of 0.7 mg of the compund (38) in 0.5 ml of dry dichlorometane, and the mixture was stirred at 20° C. for 20 minutes. The reaction mixture was neutralized with aqueous sodium bicarbonate solution and extracted with diethyl ether. The extract was worked up in a customary manner to give 0.6 mg (yield about 80%) of a crude produce (27). Without isolation of the the compound (27), the crude product was used in the subsequent desilylation.

EXAMPLE 43-h

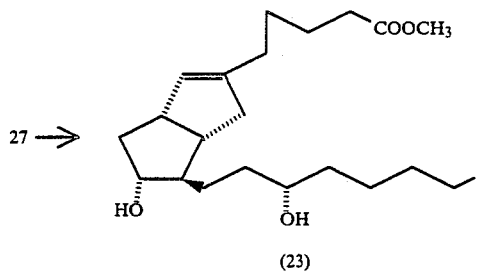

(23)

Purified isocarbvacyclin methyl ester bis-11,15-t-butyldimethylsilyl ether (27) (0.6 mg) was dissolved in 0.5 ml of THF, and 50 microliters of tetra-n-butyl ammonium fluoride (0.5M THF solution) was added, and the mixture was stirred at room temperature for 12 hours. The reaction mixture was mixed with 3 ml of saturated aqueous sodium chloride solution, and extracted three times with 5 ml of diethyl ether. The ether layers were worked up in a customary manner to give a crude product. The crude product was purified by column chromatography (silica gel 1 g; hexane:ethyl acetate=3:2→1:1) to give 0.3 mg (yield 90%) of the product (23) having the following spectral data.

$^1$H NMR (270 MHz, CDCl$_3$)δ: 0.7–0.1 (m 3, CH$_3$), 1.0–1.8 (m, 15, CH$_2$×6, CH, OH×2), 1.8–2.2 (m, 15, CH$_2$C(0), C(7)H$_2$C(12)H), 2.2–2.5 (m, 4, C(5)H$_2$C(10)H$_2$), 2.9–3.1 (m, 1, C(9)H), 3.67 (s, 3, OCH$_3$), 3.7–3.9 (m, 1, C(15)H), 4.0–4.2 (m, 1, C(11)H), 5.30 (br, s, 1 olefin in ring), 5.4–5.7 (m, 2, olefin in chain).

EXAMPLE 43-i

In the same way as in Example 43-g, 9.0 mg of the compound (38) was stirred with 120 microlieters of a 50% dichloromethane solution of trifluoroacetic acid at 30° C. for 90 minutes. The reaction was treated in a customary manner to form a crude product. The crude product was dissolved in 1 ml of THF and reacted with 0. ml of n-Bu$_4$NF (10.5M THF solution) at room temperature for 8 hours. After the reaction, the reaction mixture was worked up as in Example 43-h to give 2.7 mg (yield 62%) of the desired product (23).

EXAMPLE 44

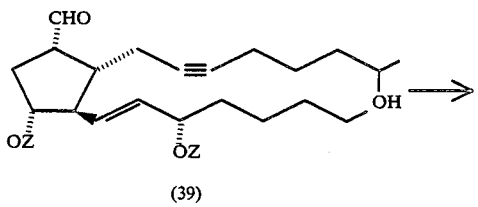

(39)

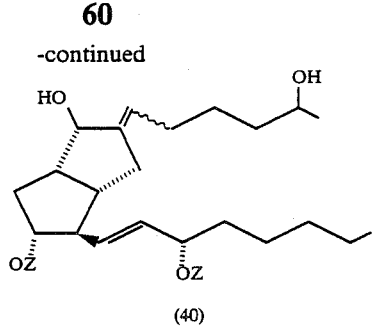

(40)

THF (5 ml) was added to 100 mg (3.6 mmoles) of a mineral oil dispersion of lithium (content 25%; containing 1% of sodium), and 500 mg (3.9 mmoles) of naphthalene was added. The mixture was stirred for 2 hours under ice cooling to prepare an anion radical solution. The solution was cooled to −78° C., and a solution of 44 mg (74 micromoles) of 11,15-bis(t-butyldimethylsilyl)-1-nor-1-(1-hydroxyethyl)-5,6-dehydro-9-deoxy-9-formylprostaglandin E$_2$ and 130 microlieters of t-butyl alcohol. The mixture was stirred for 5 minutes, and aqueous ammonium chloride solution was added. The mixture was extracted three times with 50 ml of ethyl acetate. The organic layers were washed with aqueous sodium chloride solution, dried over anhydrous magnesium sulfate, and concentrated under reduced pressure to give a crude product. The crude product was purified by silica gel column chromatography to give 23 mg (39 micromoles; yield 53%) of 11,15-bis(t-butyldimethylsilyl)-1-nor-1-(1-hydroxsyethyl)-9-hydroxycarbacyclin (40).

TLC:Rf=0.32 (n-hexane:ethyl acetate=1:1).

NMR (CDCl$_3$, ppm)δ: 0.03 (12H, s), 0.7–1.0 (21H), 1.0–2.4 (24H, m), 3.3–4.5 (6H, m), 5.3–5.6 (3H, m).

IR (liquid film): 3380, 3080, 1260, 835, 775, 740 cm$^{-1}$.

FD-MS: 595 (M+1), 594 (M+), 577 (M-17), 537 (M-57).

EI-MS: 576 (M-18, 8), 519 (34), 505 (10), 462 (4), 445 (16), 427 (9), 405 (31), 387 (22), 373 (16), 313 (56), 295 (39), 241 (30), 215 (88), 199 (40), 163 (73), 147 (100), 131 (54), 105 (69).

What is claimed is:

1. A novel isocarbacyclin which is a compound represented by the following formula [I]

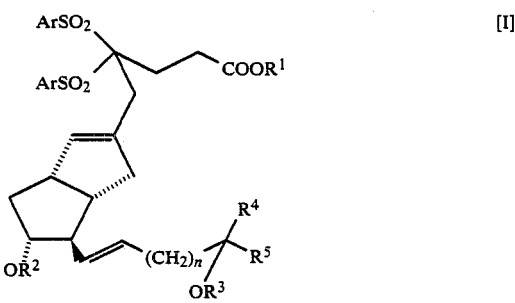

wherein R$^1$ represents a hydrogen atom, or a C$_1$–C$_4$ alkyl or alkenyl group; R$^2$ and R$^3$ are identical or different and each represents a hydrogen atom, a tri(C$_1$–C$_7$-)hydrocarbon-silyl group or a group forming an acetal linkage together with the oxygen atom of the hydroxyl group; R$^4$ represents a hydrogen atom, a methyl group or a vinyl group; R$^5$ represents an unsubstituted linear or branched C$_3$–C$_8$ alkyl group which may be interrupted by an oxygen atom, a substituted linear or branched $C_1$–$C_5$ alkyl group in which the substituent is a $C_1$–$C_6$ alkoxy group or a phenyl, phenoxy or $C_3$–$C_{10}$ cycloalkyl group which may be substituted further, a phenyl group which may be substituted, a phenoxy group which may be substituted, or a $C_3$–$C_{10}$ cycloalkyl group which may be substituted; n is 0 or 1; and Ar represents a substituted or unsubstituted phenyl group, its enantiomorph, or a mixture both in an arbitrary ratio.

2. The isocarbacyclin of claim 1 wherein $R^1$ represents a hydrogen atom, a methyl group or an allyl group.

3. The isocarbacyclin of claim 1 wherein $R^2$ and $R^3$ are identical or different, and each represents a hydrogen atom, a trimethylsilyl group, a dimethyl-t-butylsilyl group, a tetrahydropyranyl group or a methoxymethyl group.

4. The isocarbacyclin of claim 1 wherein $R^4$ represents a hydrogen atom.

5. The isocarbacyclin of claim 1 wherein $R^5$ represents a butyl, pentyl, hexyl, heptyl, 2-hexyl, 2-methyl-2-hexyl, 2-methylbutyl, 2-methylpentyl, cyclopentyl, cyclohexyl, phenyl, phenoxy, cyclopentylmethyl or cyclohexylmethyl group.

6. The isocarbacyclin of claim 1 wherein n is 0.

7. The isocarbacyclin of claim 1 wherein Ar is a phenyl or p-tolyl group.

* * * * *